US008945587B2

(12) United States Patent
Trent et al.

(10) Patent No.: US 8,945,587 B2
(45) Date of Patent: Feb. 3, 2015

(54) SYNTHETIC LIPID BIOLOGY FOR COMBINATORIAL ENGINEERING OF ENDOTOXIN

(71) Applicant: Board of Regents, The University of Texas System, Austin, TX (US)

(72) Inventors: M. Stephen Trent, Cedar Park, TX (US); Brittany Needham, Austin, TX (US); David Giles, Chattanooga, TN (US); Marvin Whiteley, Cedar Park, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 13/780,805

(22) Filed: Feb. 28, 2013

(65) Prior Publication Data

US 2013/0230555 A1  Sep. 5, 2013

Related U.S. Application Data

(60) Provisional application No. 61/604,306, filed on Feb. 28, 2012.

(51) Int. Cl.

| *A01N 63/00* | (2006.01) |
| *A01N 65/00* | (2009.01) |
| *A61K 39/02* | (2006.01) |
| *A61K 39/108* | (2006.01) |
| *C12N 15/70* | (2006.01) |
| *C12P 7/64* | (2006.01) |
| *C08B 37/00* | (2006.01) |
| *A61K 39/00* | (2006.01) |

(52) U.S. Cl.
CPC ............... *C12N 15/70* (2013.01); *C12P 7/6481* (2013.01); *C08B 37/00* (2013.01); *A61K 39/0258* (2013.01); *A61K 2039/522* (2013.01); *A61K 2039/523* (2013.01)
USPC ..... 424/241.1; 424/1.11; 424/1.17; 424/93.1; 424/93.2; 424/93.4; 424/184.1; 424/200.1; 424/234.1; 424/235.1; 424/278.1; 424/282.1

(58) Field of Classification Search
CPC .......... C12N 1/00; C12N 15/00; C12N 15/09; C12N 15/64; C12N 15/66; C12N 15/70; C12N 15/79; C07K 14/195; A61K 39/40; G06F 19/18
See application file for complete search history.

(56) References Cited

FOREIGN PATENT DOCUMENTS

WO  WO 2011/113003  *  9/2011 ............... C12N 1/20

OTHER PUBLICATIONS

Herrera et al., (Mol. Microbio. 2010. vol. 76(6): 1444-1460).*

(Continued)

*Primary Examiner* — Ja'Na Hines
(74) *Attorney, Agent, or Firm* — Parker Highlander PLLC

(57) ABSTRACT

The present disclosure generally relates to genetic engineering of bacteria. More particularly, the present disclosure relates to genetic engineering of Gram-negative bacteria expressing different species of lipid A on their surface. In one embodiment, the present disclosure provides for an engineered strain of *E. coli* according to Table 1. In another embodiment, the present disclosure provides for a lipopolysaccharide purified from an engineered strain of *E. coli* according to Table 1.

Figure 1:
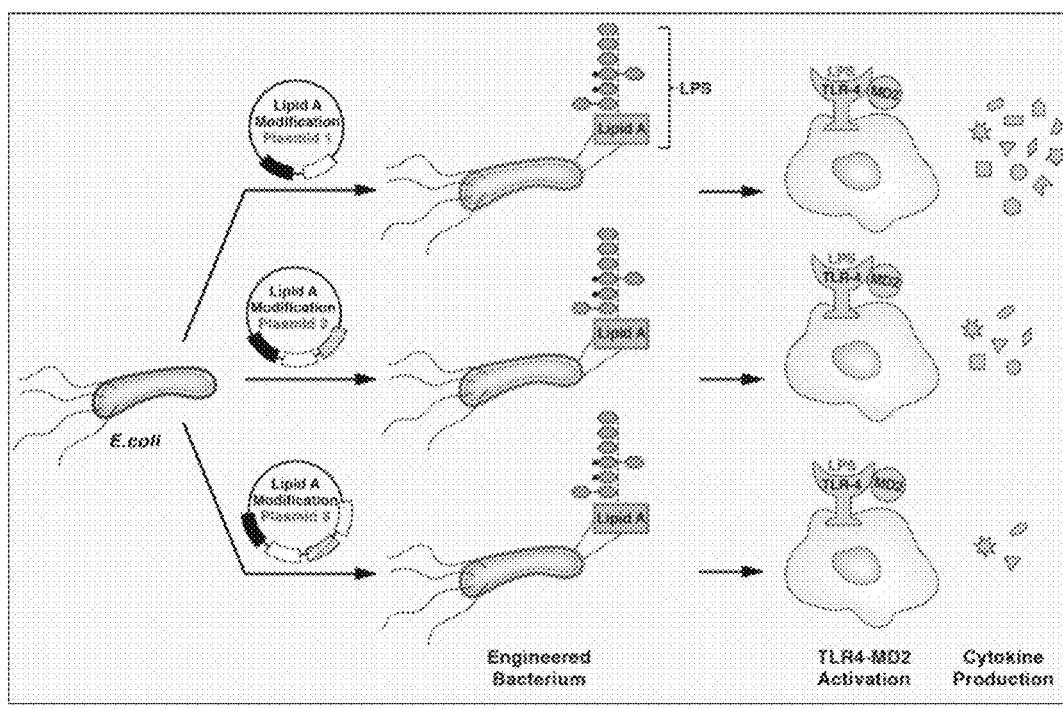

13 Claims, 36 Drawing Sheets
(12 of 36 Drawing Sheet(s) Filed in Color)

(56) References Cited

OTHER PUBLICATIONS

Cognet, et al., "Expression of recombinant proteins in a lipid A mutant of *Escherichia coli* BL21 with a strongly reduced capacity to induce dendritic cell activation and maturation," *Journal of Immunological Methods,* 272:199-210, 2003.

Herrera, et al., "Activation of PmrA inhibits LpxT-dependent phosphorylation of lipid A promoting resistance to antimicrobial peptides," *Molecular Microbiology,* 76:1444-60, 2010.

Needham, et al., "Modulating the innate immune response by combinatorial engineering of endotoxin," *PNAS,* 110:1464-9, 2013.

Park, et al., "The structural basis of lipopolysaccharide recognition by the TLR4-MD-2 complex," *Nature,* 458:1191-5, 2009.

PCT International Search Report and Written Opinion, issued in Application No. PCT/US2013/028281, dated May 22, 2013.

Touzé, et al., "Periplasmic phosphorylation of lipid A is linked to the synthesis of undecaprenyl phosphate," *Molecular Microbiology,* 67:264-77, 2008.

\* cited by examiner

4'-monophosphoryl
lipid A (*E. coli*)

3-O-deacyl-4'-monophosphoryl
lipid A (MPL™)

FIGURE 12

C

| | BN1 pE | BN1 pER | BN1 pELP | BN1 pELR | BN1 pPR | BN1 pLPR | BN2 | BN2 pEF | BN2 pEL | BN2 pFL | BN2 pEP |
|---|---|---|---|---|---|---|---|---|---|---|---|
| G-CSF | 3.01E-02 | 6.21E-07 | 4.99E-03 | 1.64E-03 | 1.89E-05 | 1.63E-03 | 4.38E-07 | 4.38E-07 | 4.38E-07 | 4.38E-07 | 1.63E-03 |
| IL-1B | 3.57E-02 | 7.77E-05 | 3.49E-02 | 7.84E-05 | 1.22E-03 | 1.89E-04 | 8.65E-05 | 7.19E-05 | 6.89E-05 | 7.06E-05 | 1.09E-04 |
| IL-6 | 3.74E-01 | 6.20E-10 | 1.33E-03 | 1.35E-04 | 6.83E-04 | 1.93E-04 | 1.36E-04 | 1.36E-04 | 1.36E-04 | 7.14E-10 | 1.49E-04 |
| IL-8 | 1.49E-01 | 5.42E-04 | 6.30E-01 | 1.34E-02 | 5.50E-01 | 1.38E-01 | 1.10E-03 | 3.17E-05 | 8.84E-05 | 3.02E-04 | 7.95E-02 |
| MCP-1 | 8.23E-02 | 1.09E-03 | 5.78E-03 | 1.01E-03 | 2.03E-02 | 8.45E-03 | 7.15E-04 | 7.73E-04 | 7.18E-04 | 7.87E-04 | 2.67E-03 |
| RANTES | 2.49E-02 | 8.06E-05 | 2.39E-04 | 6.15E-05 | 4.84E-04 | 1.02E-04 | 5.72E-05 | 5.63E-05 | 5.54E-05 | 5.70E-05 | 8.32E-05 |
| TNF-a | 5.38E-02 | 3.04E-05 | 7.21E-04 | 3.10E-05 | 2.50E-04 | 8.77E-05 | 2.80E-05 | 7.87E-05 | 2.81E-05 | 7.86E-05 | 4.70E-05 |

SEQUENCE LISTING

<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: Synthetic Primer

<400> SEQUENCE: 1
gcggatccat gctcaaacag acatta                26

<210> SEQ ID NO 2
<211> LENGTH: 28
<212> TYPE: DNA
<213> ORGANISM: Artificial Sequence
<220> FEATURE:
<223> OTHER INFORMATION: Synthetic Primer

<400> SEQUENCE: 2
gcgcggccgc ctaaataatc tctctatt              28

<210> SEQ ID NO 3
<211> LENGTH: 26
<212> TYPE: DNA
<213> ORGANISM: Artificial Sequence
<220> FEATURE:
<223> OTHER INFORMATION: Synthetic Primer

<400> SEQUENCE: 3
gcggatcctt ggcaagattt catatc                26

<210> SEQ ID NO 4
<211> LENGTH: 28
<212> TYPE: DNA
<213> ORGANISM: Artificial Sequence
<220> FEATURE:
<223> OTHER INFORMATION: Synthetic Primer

<400> SEQUENCE: 4
gcgcggccgc tcaatattct tttttacg              28

<210> SEQ ID NO 5
<211> LENGTH: 26
<212> TYPE: DNA
<213> ORGANISM: Artificial Sequence
<220> FEATURE:
<223> OTHER INFORMATION: Synthetic Primer

<400> SEQUENCE: 5
gcggatccat gtatatgaag agaata                26

<210> SEQ ID NO 6
<211> LENGTH: 28
<212> TYPE: DNA
<213> ORGANISM: Artificial Sequence
<220> FEATURE:
<223> OTHER INFORMATION: Synthetic Primer

<400> SEQUENCE: 6
gcgcggccgc tcagaaatta taactaat              28

<210> SEQ ID NO 7
<211> LENGTH: 26
<212> TYPE: DNA
<213> ORGANISM: Artificial Sequence

```
<220> FEATURE:
<223> OTHER INFORMATION: Synthetic Primer

<400> SEQUENCE: 7
gcgaattcat gttcgcagca atcatt                                          26

<210> SEQ ID NO 8
<211> LENGTH: 26
<212> TYPE: DNA
<213> ORGANISM: Artificial Sequence
<220> FEATURE:
<223> OTHER INFORMATION: Synthetic Primer

<400> SEQUENCE: 8
gcggatcctc agaggaggct gaaaag                                          26

<210> SEQ ID NO 9
<211> LENGTH: 26
<212> TYPE: DNA
<213> ORGANISM: Artificial Sequence
<220> FEATURE:
<223> OTHER INFORMATION: Synthetic Primer

<400> SEQUENCE: 9
gcggatccat gaacgtgagt aaatat                                          26

<210> SEQ ID NO 10
<211> LENGTH: 28
<212> TYPE: DNA
<213> ORGANISM: Artificial Sequence
<220> FEATURE:
<223> OTHER INFORMATION: Synthetic Primer

<400> SEQUENCE: 10
gcgcggccgc tcaaaactga aagcgcat                                        28

<210> SEQ ID NO 11
<211> LENGTH: 26
<212> TYPE: DNA
<213> ORGANISM: Artificial Sequence
<220> FEATURE:
<223> OTHER INFORMATION: Synthetic Primer

<400> SEQUENCE: 11
gcggatccat gaacaaatac agctat                                          26

<210> SEQ ID NO 12
<211> LENGTH: 28
<212> TYPE: DNA
<213> ORGANISM: Artificial Sequence
<220> FEATURE:
<223> OTHER INFORMATION: Synthetic Primer

<400> SEQUENCE: 12
gcgcggccgc tcagaagaag aaggtgat                                        28
```

SYNTHETIC LIPID BIOLOGY FOR COMBINATORIAL ENGINEERING OF ENDOTOXIN

This application claims the benefit of U.S. Provisional Patent Application No. 61/604,306, filed Feb. 28, 2012, incorporated herein by reference in its entirety.

STATEMENT OF GOVERNMENT INTEREST

This invention was made with government support under Grant Numbers RO1AI076322 and RO1AI075068 awarded by the National Institutes of Health. The government has certain rights in the invention.

BACKGROUND

In 1892, Richard Pfeiffer introduced the revolutionary concept of bacterial endotoxin in his description of a non-proteinaceous, non-secreted toxin bound to the surface of *Vibrio cholerae* (Pfeiffer et al., 1892). This toxin, now known as lipopolysaccharide (LPS), is the major surface molecule of Gram-negative bacteria that triggers the host immune response during infection (Poltorak et al., 2000; Raetz et al. 2002). LPS is composed of lipid A, core oligosaccharide, and O-antigen (Raetz et al., 2007). The bioactive domain of LPS is lipid A, or endotoxin (Raetz et al. 2002). Lipid A is recognized by the innate immune system through the conserved pattern recognition receptor, Toll-like receptor 4/myeloid differentiation factor 2 (TLR4/MD-2) complex, which initiates a robust signal cascade that leads to production of inflammatory cytokines This signaling is crucial for detection and clearance of infection, but can be potent enough to result in lethal endotoxic shock (Raetz et al. 2002). Such tremendous immunogenicity makes LPS an attractive therapeutic tool, but its toxicity is a major concern.

Efforts have been made to dampen the toxicity of whole bacteria by altering the degree of LPS acylation. One approach has been to inactivate lpxM, a gene encoding the acyltransferase responsible for converting lipid A from a penta-acylated to a hexa-acylated species. LpxM mutants are under investigation in the development of meningococcal vaccines, oncolytic *Salmonella* strains that specifically target tumors, and bacterial strains designed for gene therapy. Other efforts to detoxify cells or outer membrane vesicles have included acyl chain modification by the enzymes PagL or PagP. However, no strains have been previously generated using a complex combinatorial approach to yield a diverse library in one species of bacterium.

A collection of LPS molecules exhibiting a wide range of toxicity would be beneficial for many biotechnological applications.

SUMMARY OF THE INVENTION

In some embodiments, the present invention provides an engineered strain of *E. coli* comprising deletions of the lpxT, eptA, and pagP genes. In certain aspects, the engineered strain may also comprise deletions of the Kan$^R$ cassette and lpxM gene. In additional aspects, the present engineered strain may comprise at least one expression vector that comprises at least one gene encoding a lipid A modification enzyme selected from the group consisting of lpxE, lpxF, lpxO, lpxR, pagL, and pagP.

In another embodiment, the present invention provides an engineered strain of *E. coli* comprising deletions of the lpxT, eptA, and pagP genes and further comprising an expression vector that comprises the lpxE, pagL, and pagP genes.

In yet another embodiment, the present invention provides an engineered strain of *E. coli* comprising deletions of the lpxT, eptA, and pagP genes and further comprising an expression vector that comprises the lpxE, pagL, lpxO, and pagP genes.

In one embodiment, the present invention also provides a method for synthesizing 3-O-deacyl-4'-monophosphoryl lipid A without the need for acid and base treatment of the synthesized lipid A. Said method comprises providing at least one engineered bacterium of *E. coli* comprising deletions of the lpxT, eptA, and pagP genes, introducing the bacterium to a plasmid comprising an expression vector that comprises the lpxE, pagL,and pagP genes or an expression vector that comprises the lpxE, pagL, lpxO, and pagP genes, and allowing the engineered bacterium to grow under conditions to produce 3-O-deacyl-4'-monophosphoryl lipid A.

In certain embodiments, the present invention provides a lipopolysaccharide purified from an engineered strain of *E. coli* comprising deletions of the lpxT, eptA, and pagP genes and further comprising at least one expression vector that comprises at least one gene encoding a lipid A modification enzyme selected from the group consisting of lpxE, lpxF, lpxO, lpxR, pagL, and pagP, wherein said strain may or may not comprise deletions of the Kan$^R$ cassette and lpxM gene.

In certain embodiments, the present invention provides a vaccine adjuvant comprising a lipopolysaccharide purified from an engineered strain of *E. coli* comprising deletions of the lpxT, eptA, and pagP genes and further comprising at least one expression vector that comprises at least one gene encoding a lipid A modification enzyme selected from the group consisting of lpxE, lpxF, lpxO, lpxR, pagL, and pagP, wherein said strain may or may not comprise deletions of the Kan$^R$ cassette and lpxM gene.

In certain embodiments, the present invention provides a whole cell vaccine comprising an engineered strain of *E. coli* comprising deletions of the lpxT, eptA, and pagP genes and further comprising at least one expression vector that comprises at least one gene encoding a lipid A modification enzyme selected from the group consisting of lpxE, lpxF, lpxO, lpxR, pagL, and pagP, wherein said strain may or may not comprise deletions of the Kan$^R$ cassette and lpxM gene, and wherein said vaccine further comprises a pharmaceutically acceptable excipient or carrier.

DRAWINGS

Some specific example embodiments of the disclosure may be understood by referring, in part, to the following description and the accompanying drawings. The patent or application file contains at least one drawing executed in color. Copies of this patent or patent application publication with color drawing(s) will be provided by the Office upon request and payment of the necessary fee.

FIG. 1 shows combinatorial engineering of lipid A anchors to generate diverse immune responses. The outer surface of *E. coli* strains varies in LPS structure when plasmids are expressed that contain combinations of lipid A modifying enzymes. The altered LPS molecules bind and activate the TLR4/MD-2 complex differentially, altering the nature of downstream cytokine production.

Figure 2:
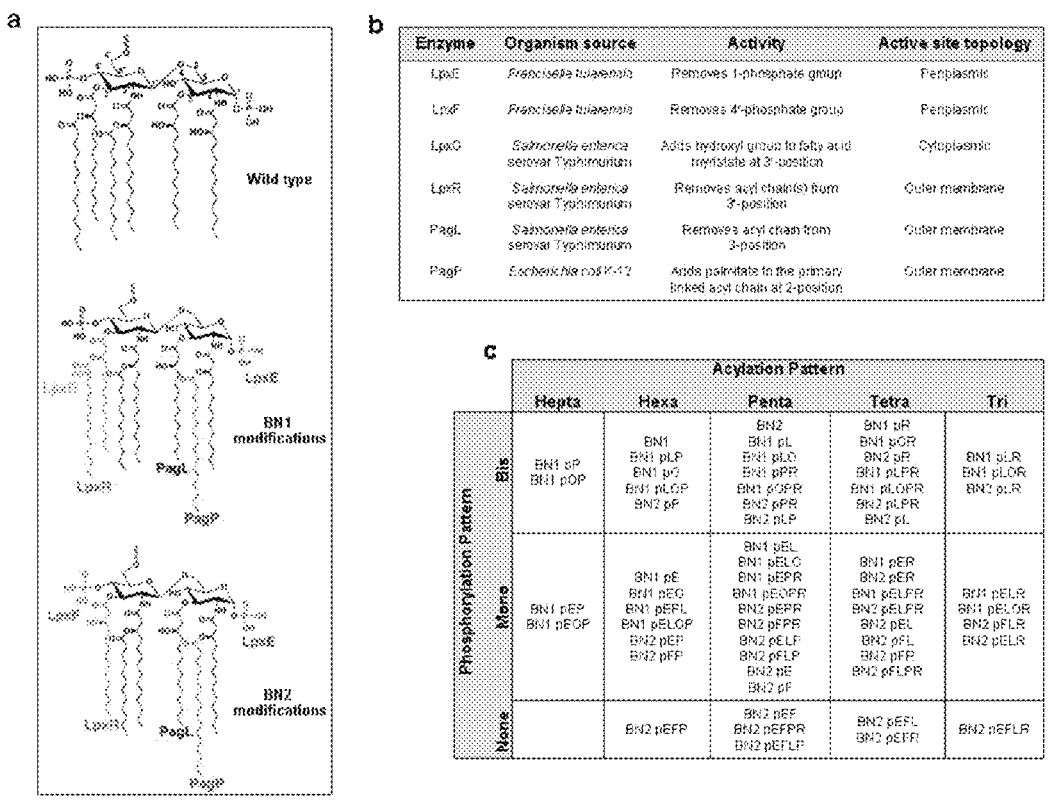

FIG. 2 shows modification machinery used for generation of engineered lipid A molecules in whole bacteria. Lipid A structures of wild type *E. coli* K12, BN1, and BN2 are shown with the names of the 6 lipid A modifying enzymes represented next to the group that each enzyme modifies (a). LpxR, PagL, LpxE, and LpxF (as indicated) all remove the corresponding acyl chain or phosphate group. LpxO and PagP transfer the hydroxyl or acyl chain onto the molecule, respectively. The attachment site for remaining polysaccharide is indicated at the 6'-position of each molecule. The organism source, enzyme activity, and active site topology of each of the 6 enzymes is presented (b), and the chart shows the 61 combinatorial strains, organized according to acylation and phosphorylation patterns (c). Combinatorial strains were generated by transformation of BN1 and BN2 with a pQLinkN plasmid expressing combinations of the 6 lipid A modifying enzymes. Each enzyme is abbreviated by its final letter and ordered alphabetically in the plasmid name, i.e., LpxE is abbreviated E, LpxF is F, LpxR is R, PagP is P, PagL is L, and LpxO is O.

FIG. 3 shows analysis of engineered lipid A molecules. TLC of isolated lipid A from combinatorial strains is shown to illustrate the diversity within the collection (a). This method allows species separation, identification, and quantification based upon hydrophobicity-mediated migration. Mass spectrometry of isolated lipid A from selected strains allows further identification of lipid A species (b-d). BN1 pE produces a major peak at m/z 1716.8, consistent with the expected removal of one phosphate group (b). BN2 pLR produces a major peak at m/z 1133.9, corresponding to the mass of a tri-acylated lipid A molecule (c). This is contrasted with BN1 pELR (d), which produces a predominant peak at m/z 1053.6, corresponding to the dephosphorylation of the major peak seen in BN1 pLR. Minor peaks in both of these strains are similar. Peaks at m/z ~1360 and ~1570 correspond to masses of lipid A resulting from a single deacylation by either LpxR or PagL, respectively. The peak at m/z ~1796 corresponds to residual unmodified BN1 lipid A. In BN1 pLR, there is a slight loss of the labile 1-phosphate group from the major species, yielding a peak at m/z 1054.0.

Figure 4:
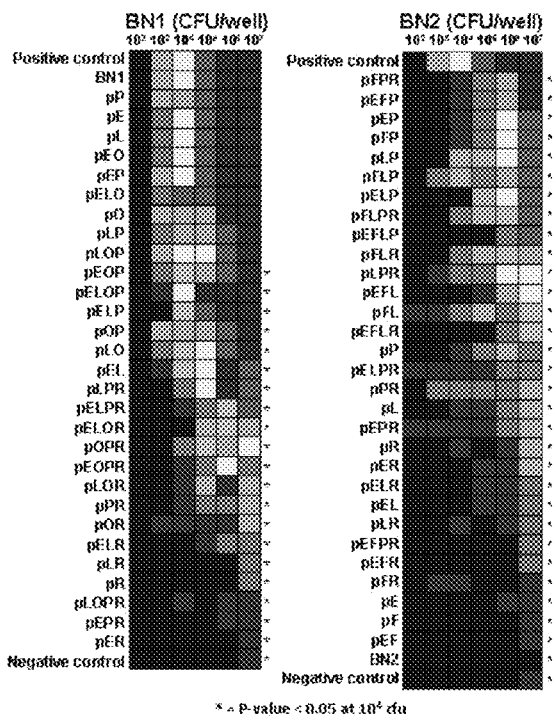
Figure 4:
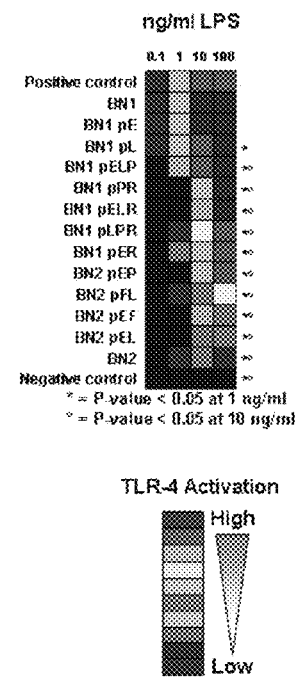

FIG. 4 shows TLR4 stimulation by whole bacterial cells and LPS. Stimulation of TLR4 following incubation of whole bacterial cells with HEK-Blue™ hTLR4 cells expressing TLR4, MD2, CD14 and the NF-κB and AP-1-dependent reporter, secreted embryonic alkaline phosphatase (SEAP) that indicates TLR4 stimulation is depicted (a). The TLR4 responses to whole cells are shown for all strains. Colors were assigned based on the TLR4 stimulation results in the BN1 strain. Rational for colorimetric designations is displayed in FIG. 10. The positive control is E. coli K12 strain W3110, the parent strain of the mutants used in this study. The negative control for this assay is strain CMR300, an E. coli strain that produces only lipid $IV_A$, a tetra-acylated TLR4 antagonist. HEK-Blue™ hTLR4 cells were also incubated with increasing concentrations of LPS from 13 of the 61 engineered strains (b). E. coli K-12 LPS was used as a positive control and R. sphaeroides LPS, a known TLR4 antagonist, served as a negative control.

Figure 5:
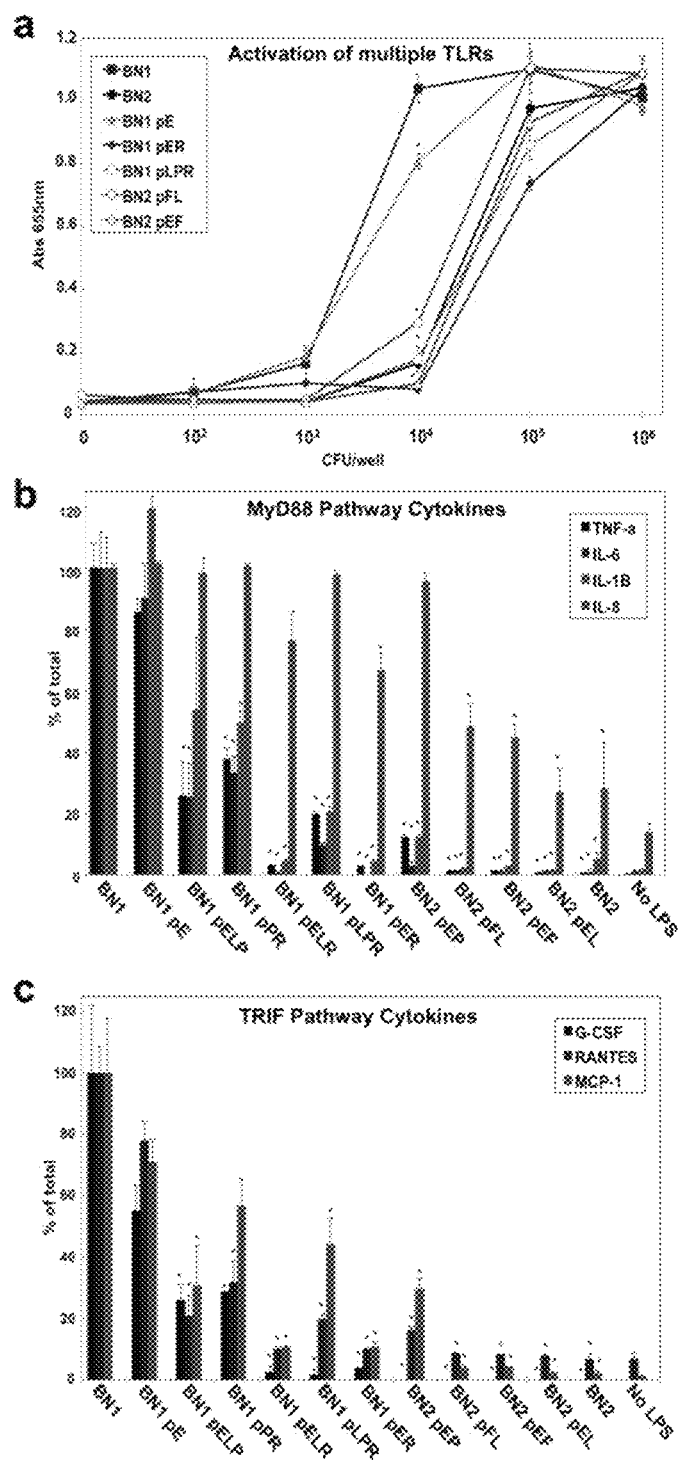

FIG. 5 shows overall stimulation of monocytes expressing multiple pattern recognition receptors. THP1-XBlue monocytes expressing all TLRs, Nod1, Nod2, MD-2, and CD14 were incubated with whole bacterial cells, and overall TLR activation was measured. The graph of representative samples illustrates that in the range of $10^3$-$10^5$ CFU/well the activation of the THP1 cells was reduced, and all samples were significantly different from BN1 at $10^4$ CFU/well (p<0.001) (a). Production of MyD88 pathway cytokines TNF-α, IL-6, IL-1β, and IL-8 from THP-1 cells incubated with 100 ng/ml LPS. Cytokine levels are presented as percent of the BN1 level (b). Production of TRIF pathway cytokines G-CSF, RANTES, and MCP-1 from THP-1 cells incubated with 100 ng/ml LPS. Cytokine levels are presented as percent of the BN1 level (c).

Figure 6:
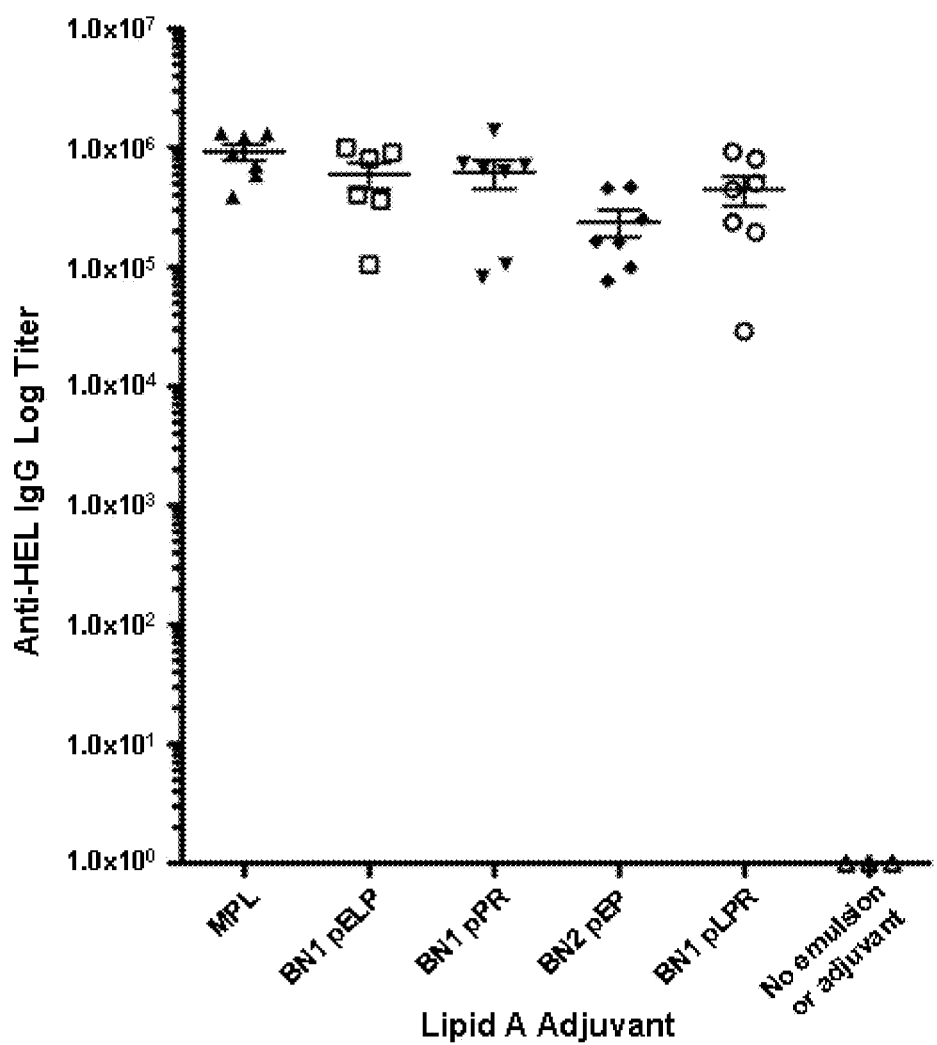

FIG. 6 shows acquired immune response to lipid A adjuvants. BALB/cJ mice were immunized with 50 μl of an emulsion of 30 μg lysozyme from chicken egg white (HEL) with 6 pM of purified lipid A and serum collected was analyzed by ELISA. All lipid A adjuvants tested (BN1 pELP, BN1 pPR, BN2 pEP, and BN1 pLPR) induced a high IgG response, and only BN2 pEP was significantly lower than the MPL™ control (P=0.0009).

Figure 7:
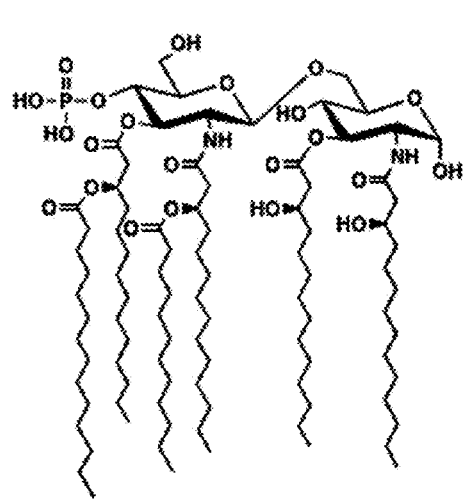
Figure 7:
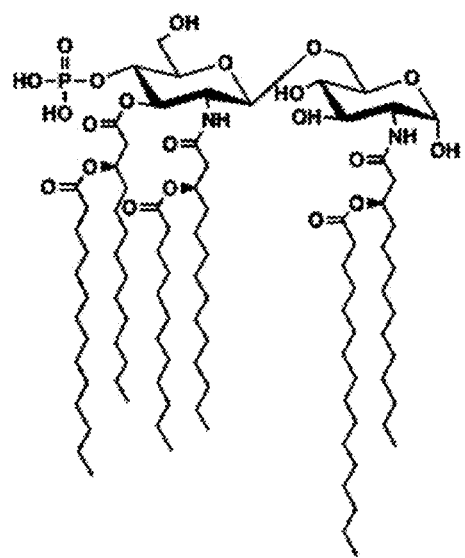

FIG. 7 shows chemical structures of 4'-monophosphoryl lipid A and of 3-O-deacyl-4'-monophosphoryl lipid A (MPL™).

Figure 8B:
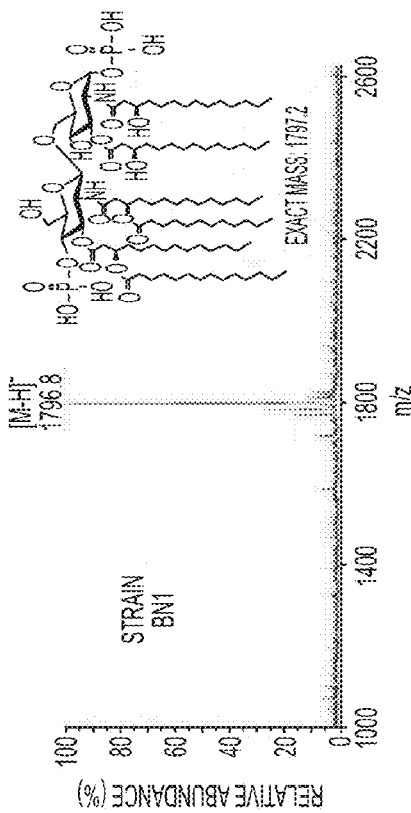
Figure 8C:
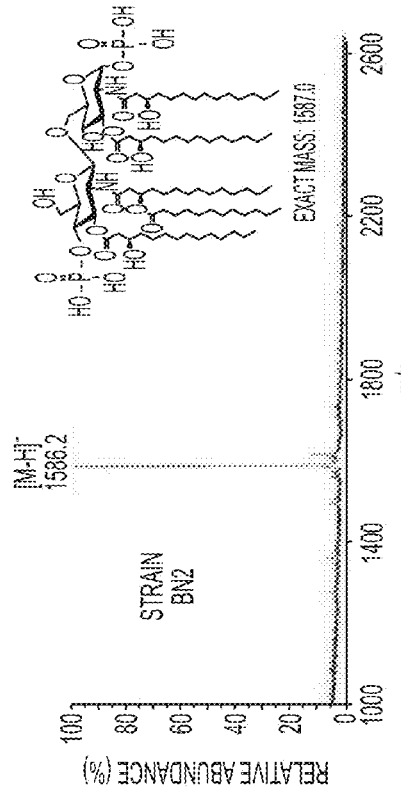

FIG. 8 shows confirmation of mutant BN1 and BN2 strains. Radiolabeled lipid A of W3110 (E. coli K12), BN1, MLK1067, and BN2 was separated by TLC (a). W3110 synthesizes hexa-acylated lipid A and either two or three phosphate groups. BN1 loses the capacity to synthesize the lipid A species with three phosphate groups. MLK1067 is an 1pxM mutant of W3110 that synthesizes penta-acylated lipid A. BN2 produces only penta-acylated, bisphosphorylated lipid A. b-c) BN1 and BN2 lipid A was analyzed by MALDI-TOF MS in negative ion linear mode. Ion peaks (±1) correspond to an appropriate exact mass for BN1 hexa-acylated lipid A with two phosphates at m/z 1797.2 (b) and BN2 penta-acylated lipid A with two phosphates at m/z 1587.0 (c).

Figure 9A:
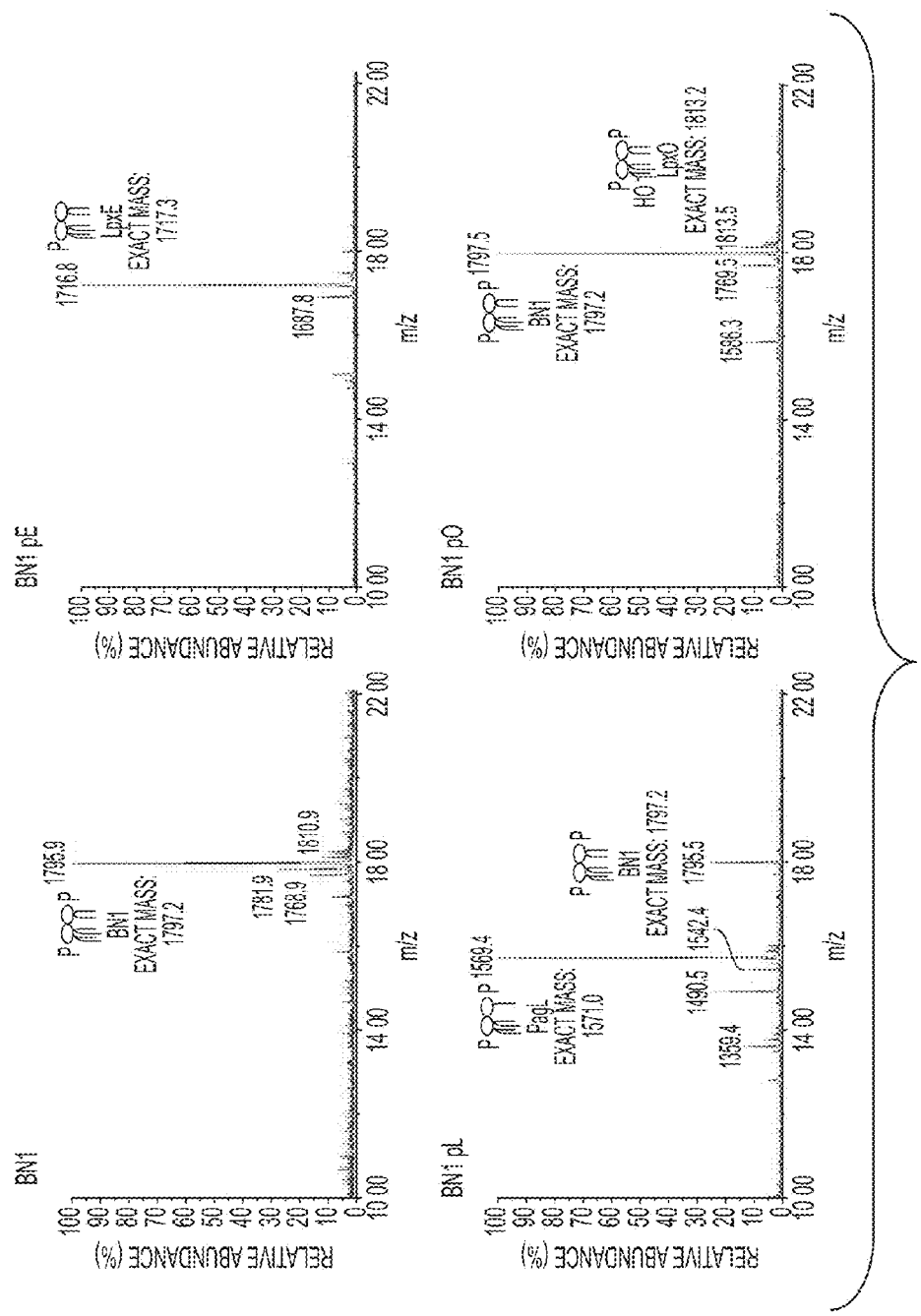
Figure 9B:
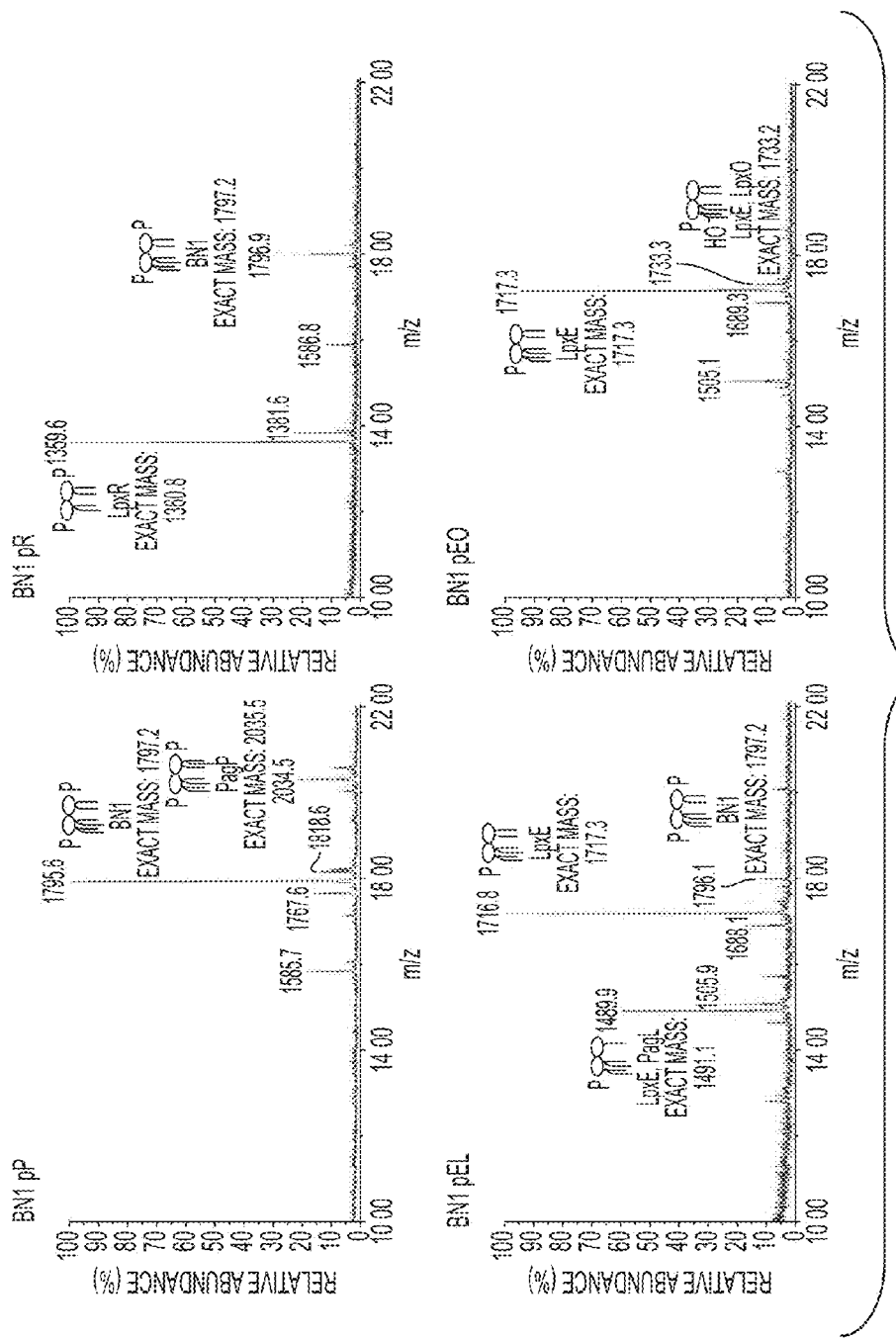
Figure 9C:
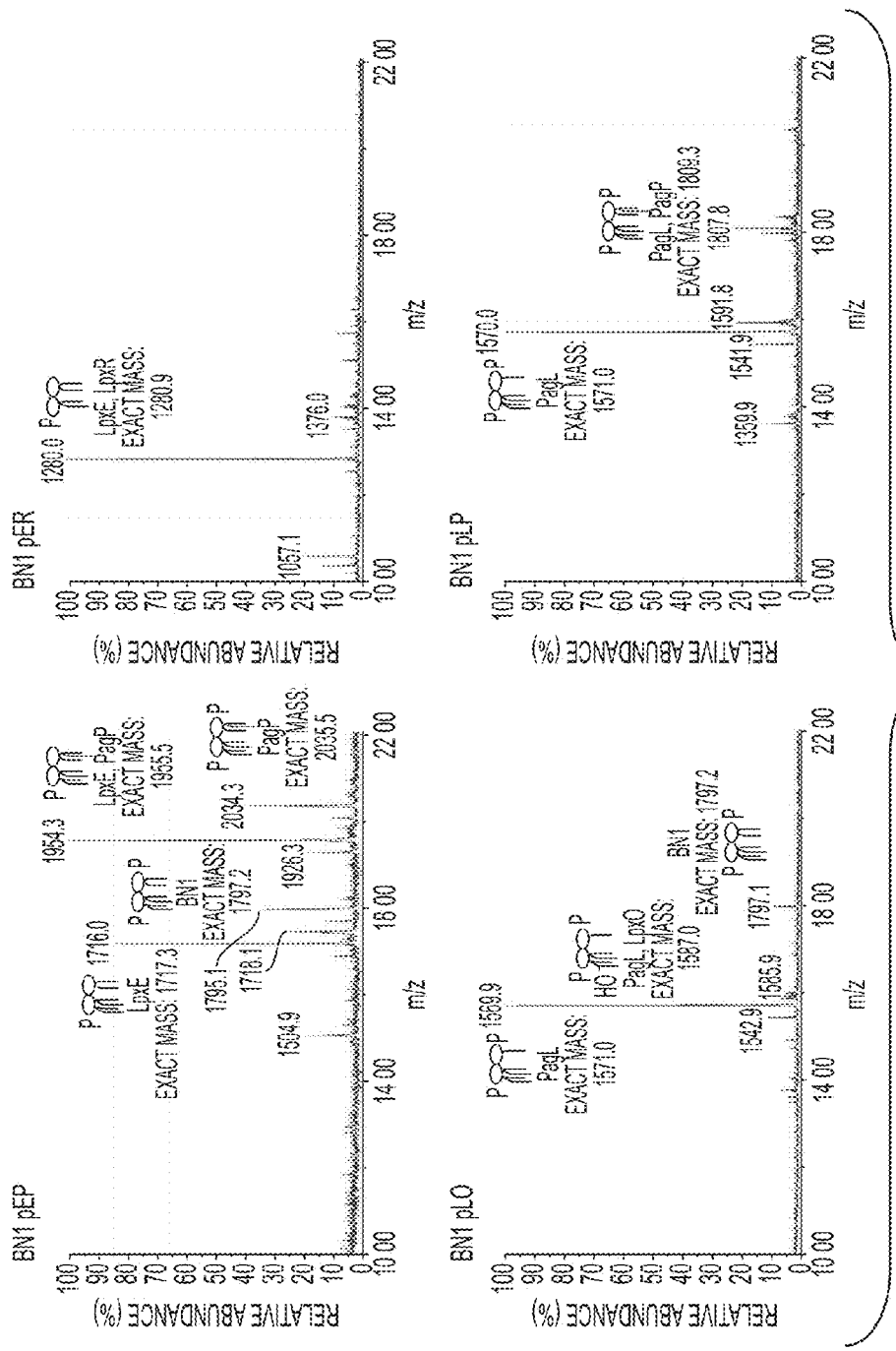
Figure 9D:
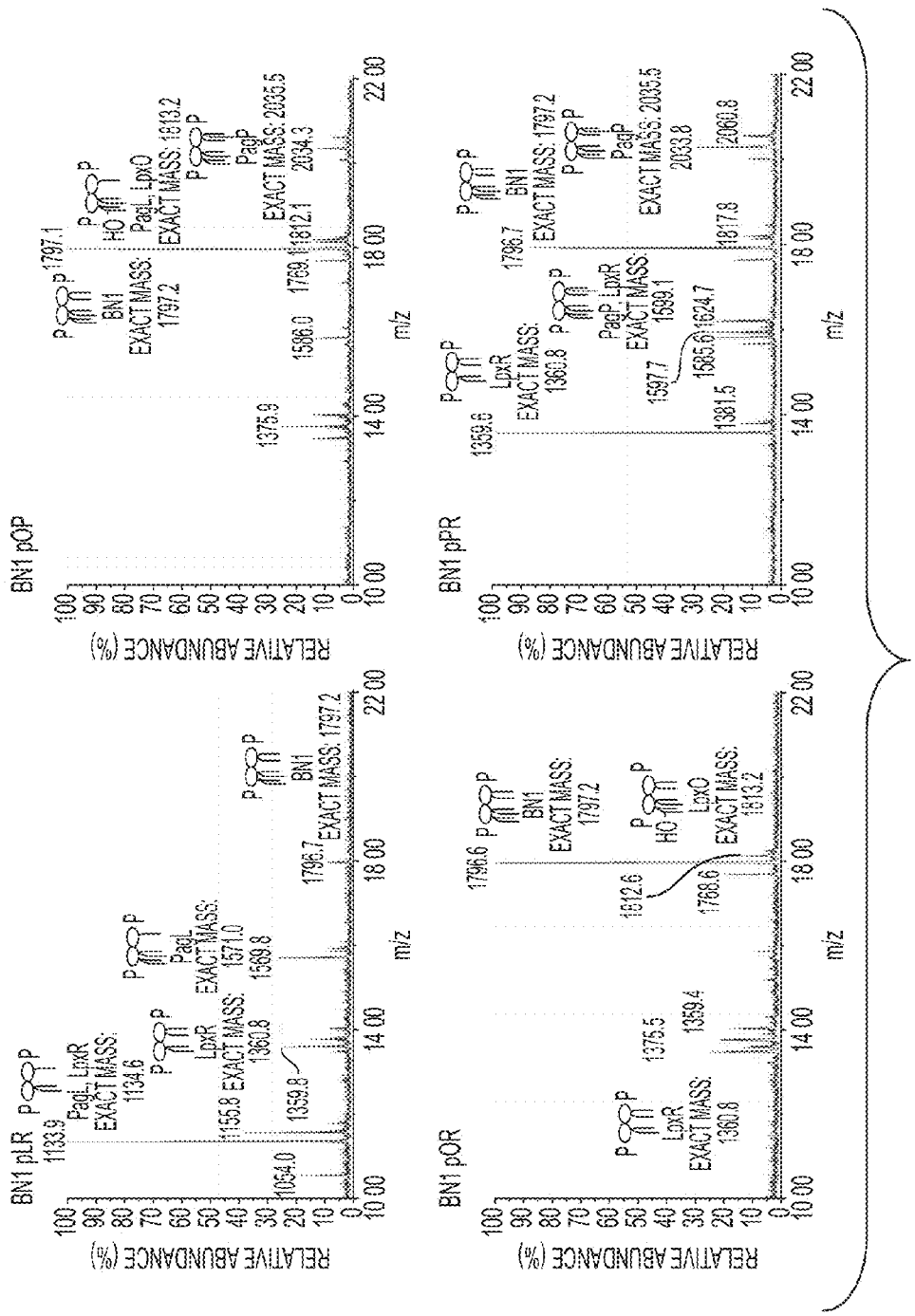
Figure 9E:
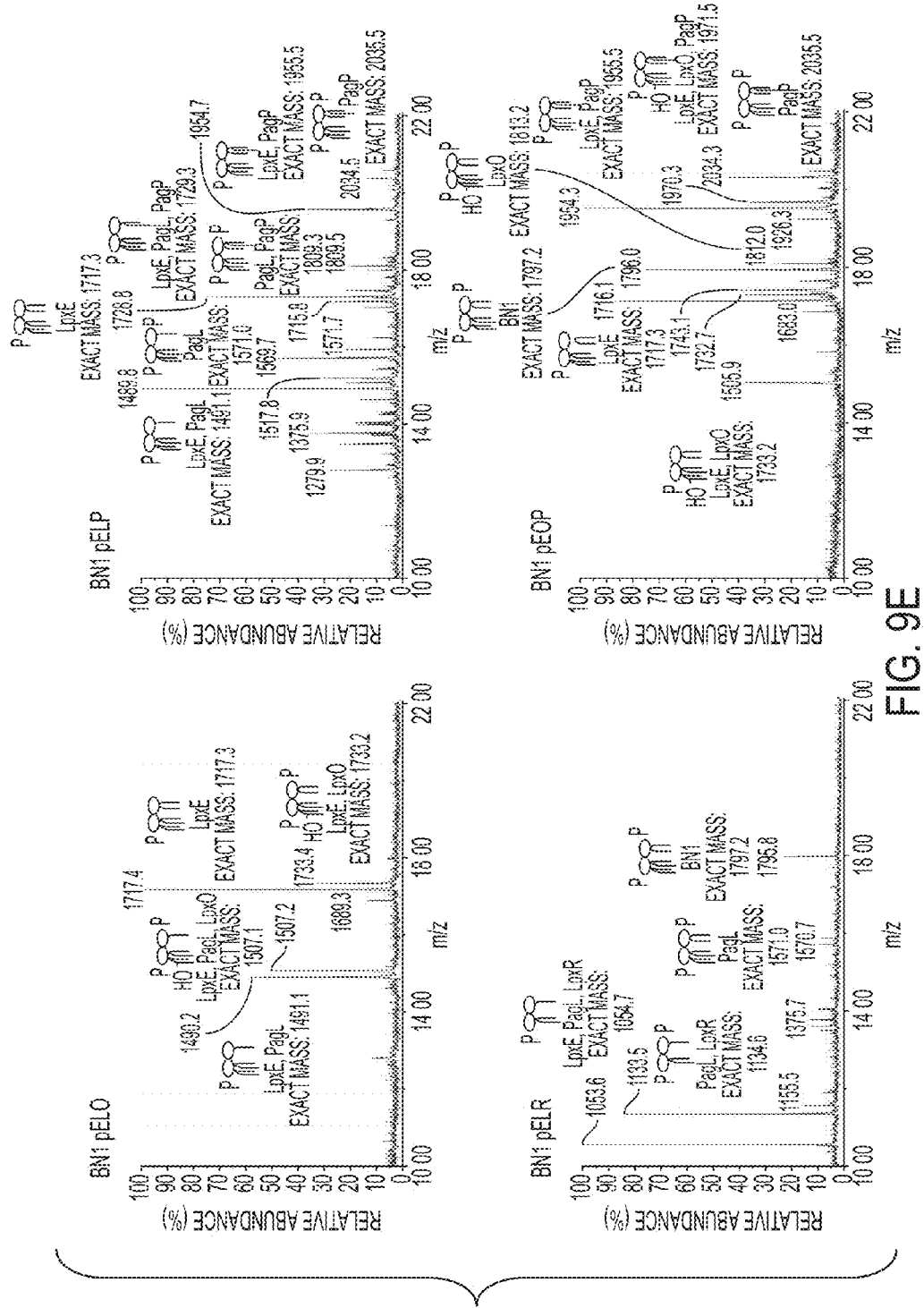
Figure 9F:
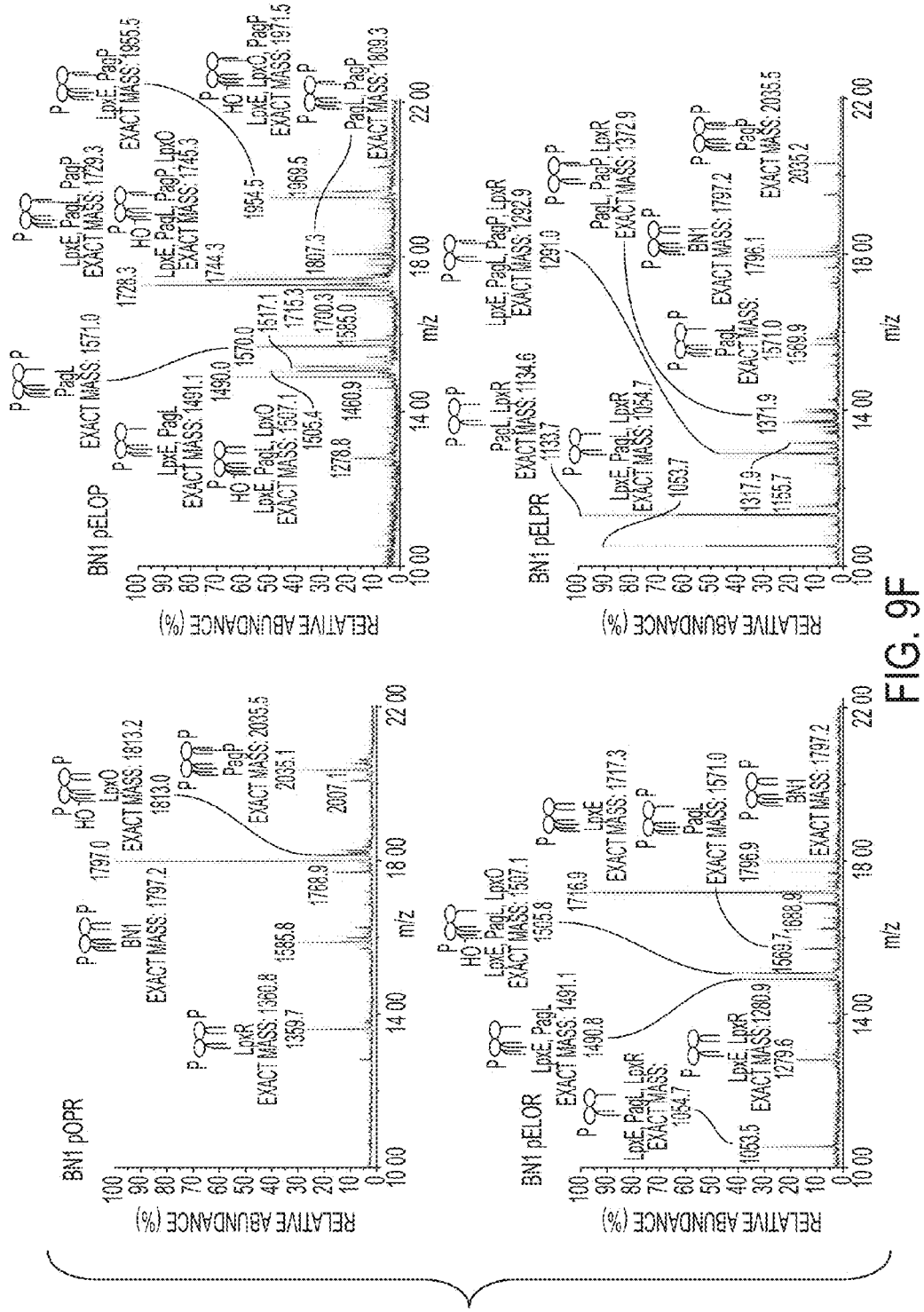
Figure 9G:
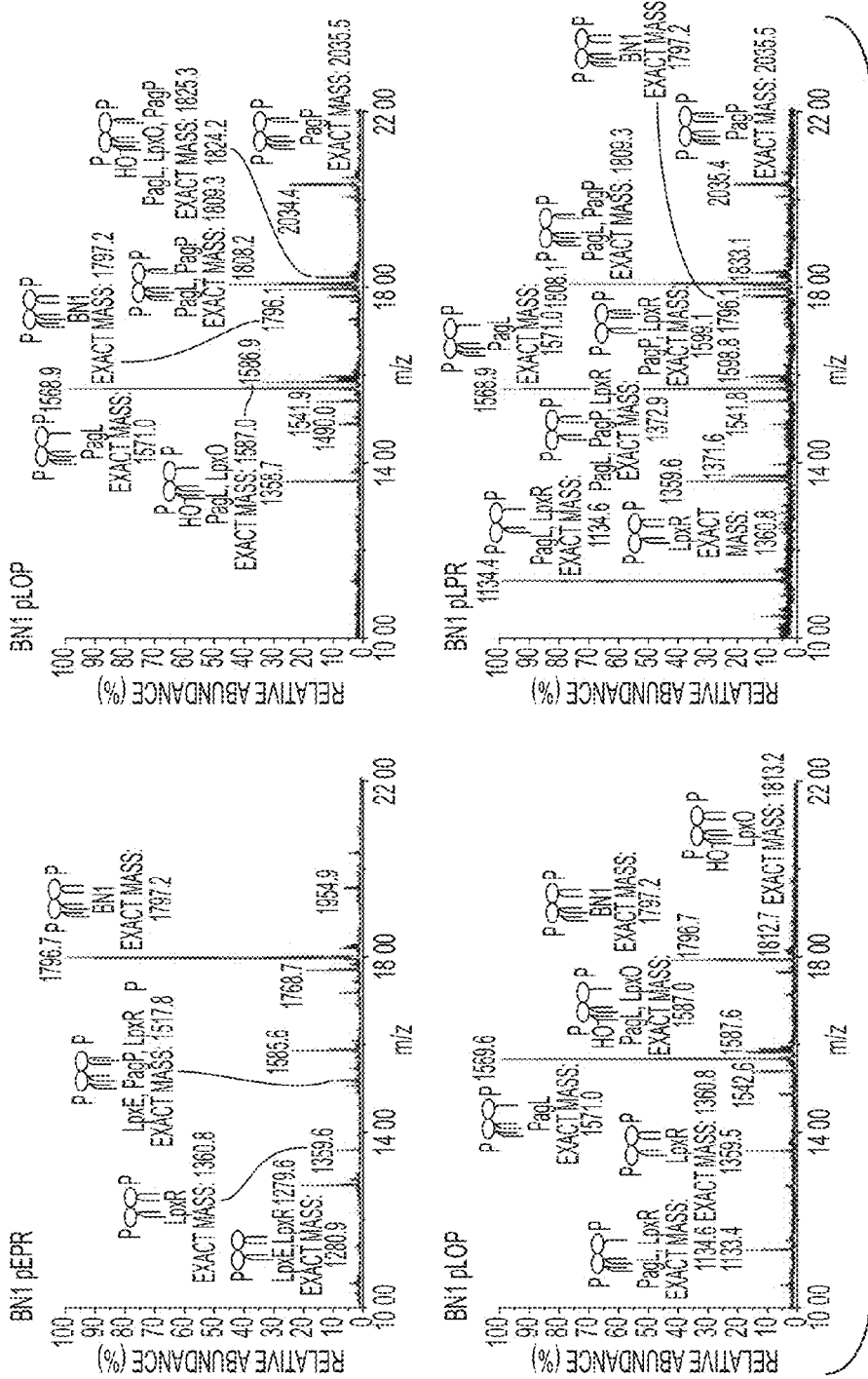
Figures 1, 9H:
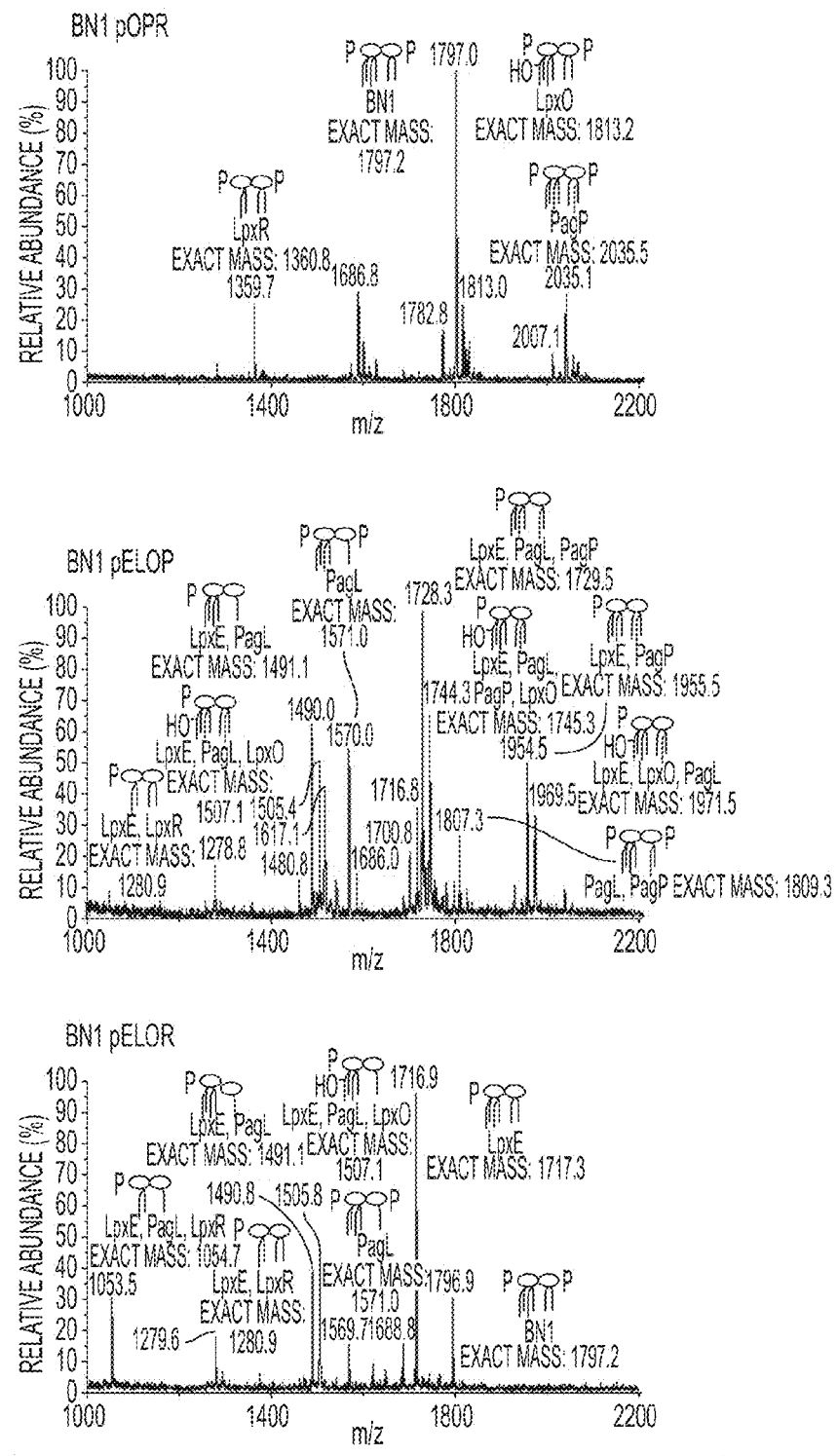
Figures 2, 9H:
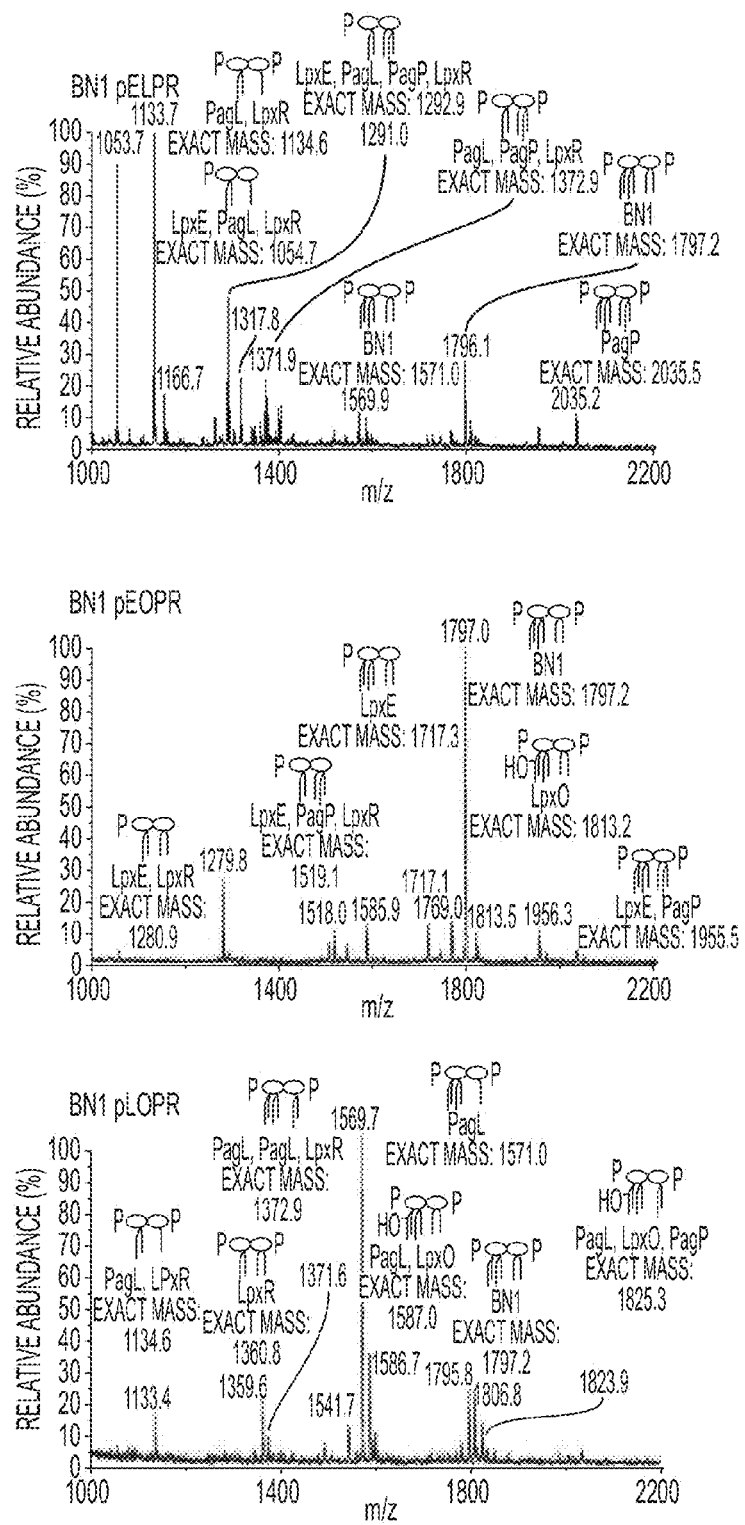
Figure 9I:
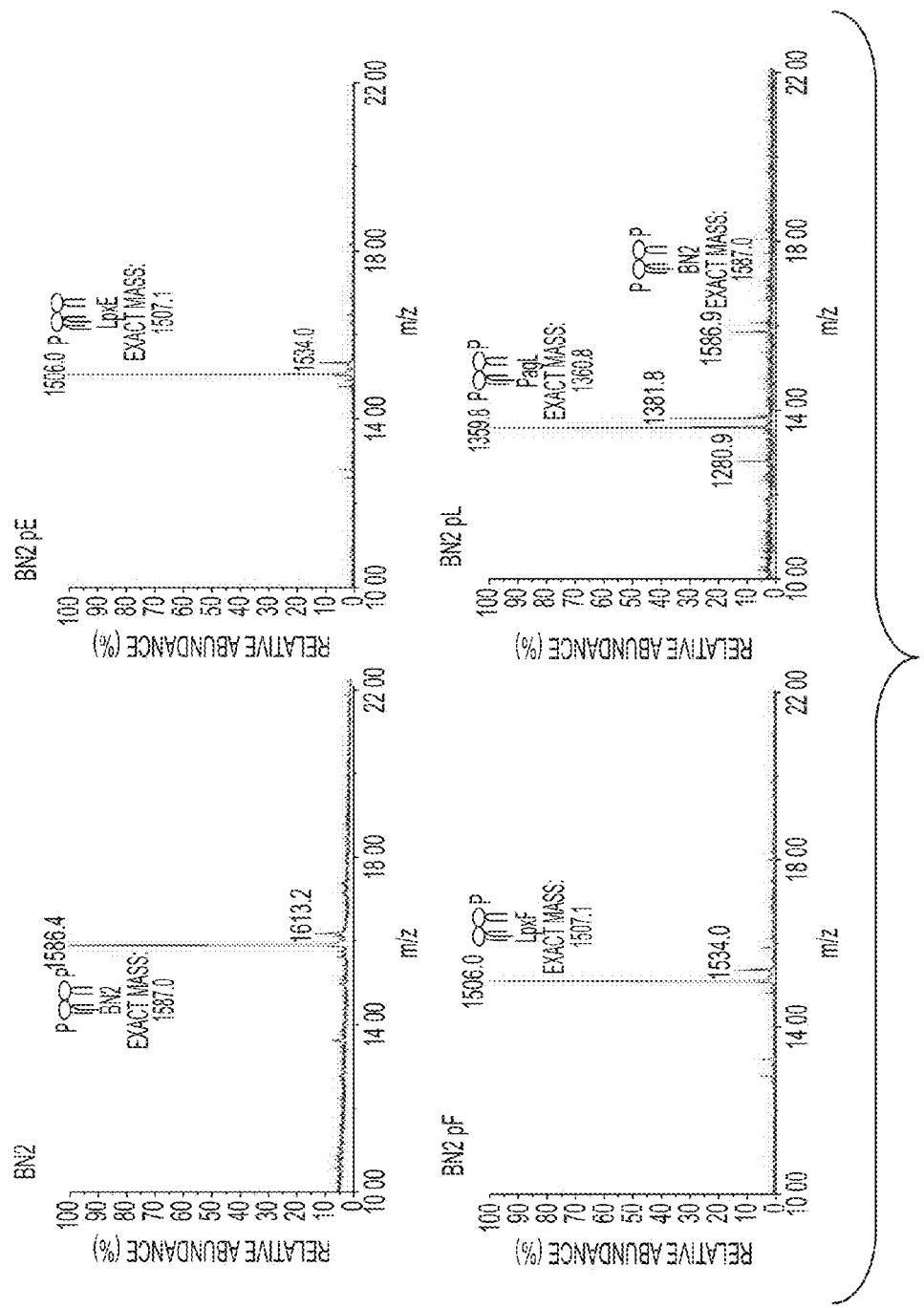
Figure 9J:
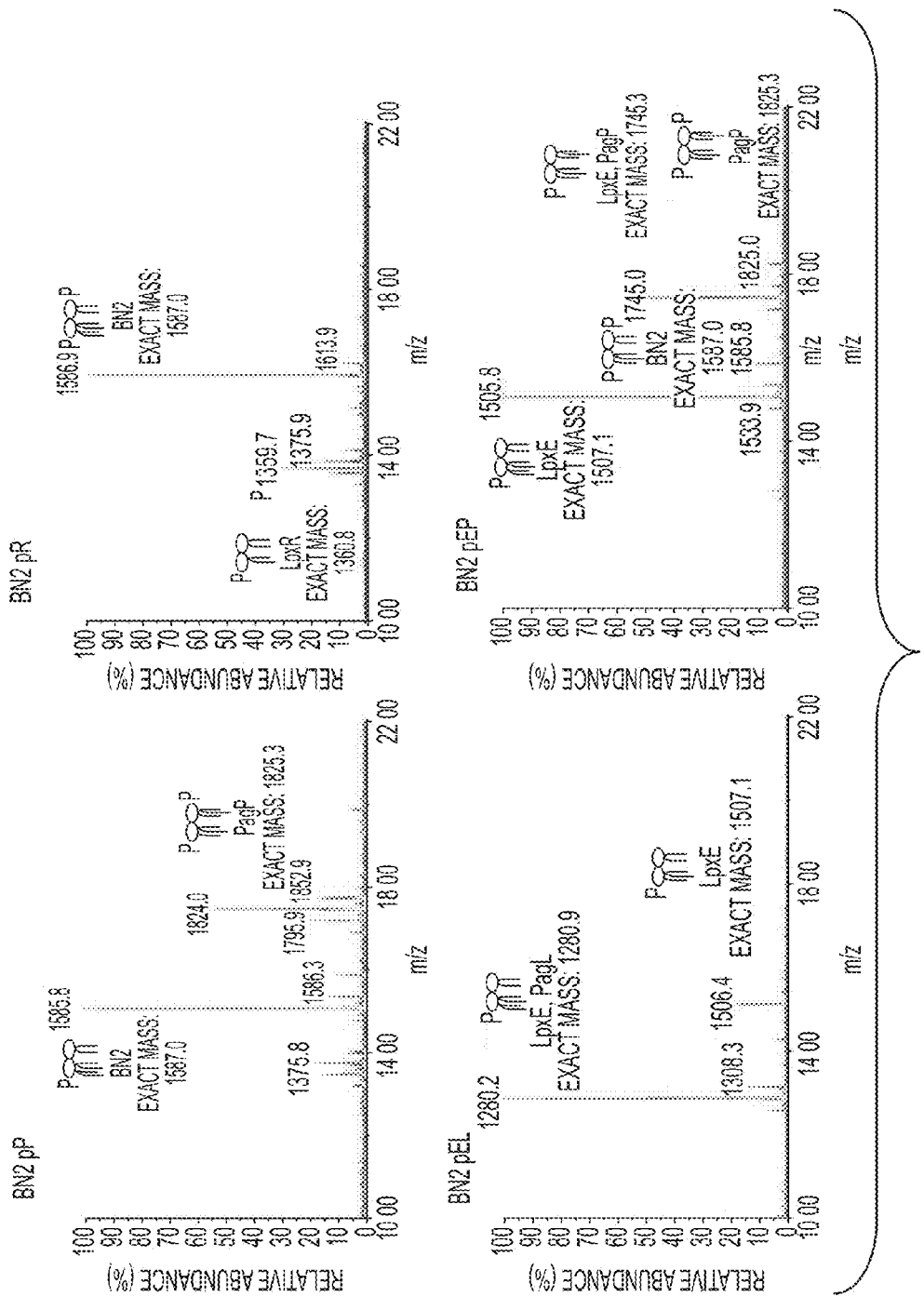
Figure 9K:
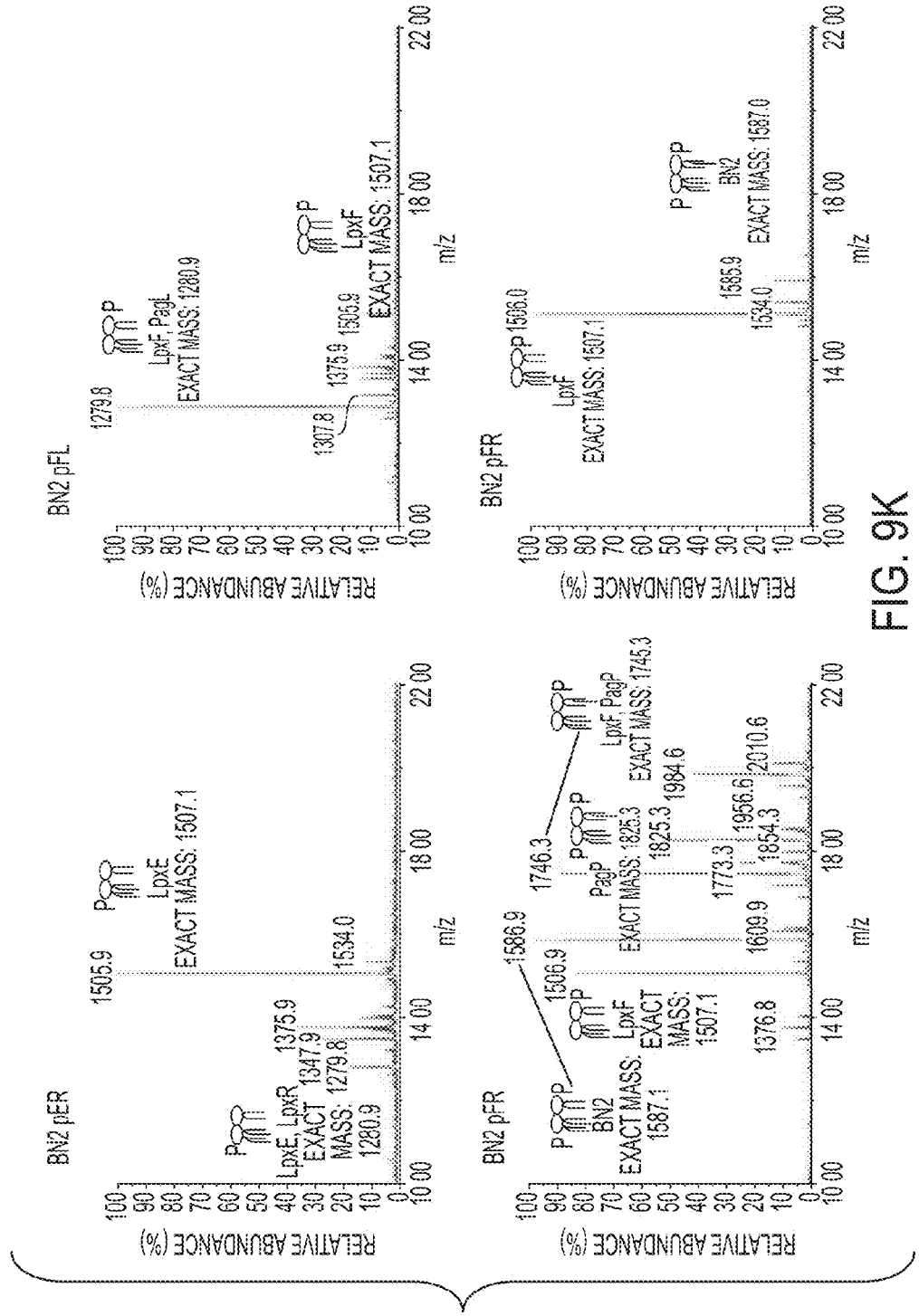
Figure 9L:
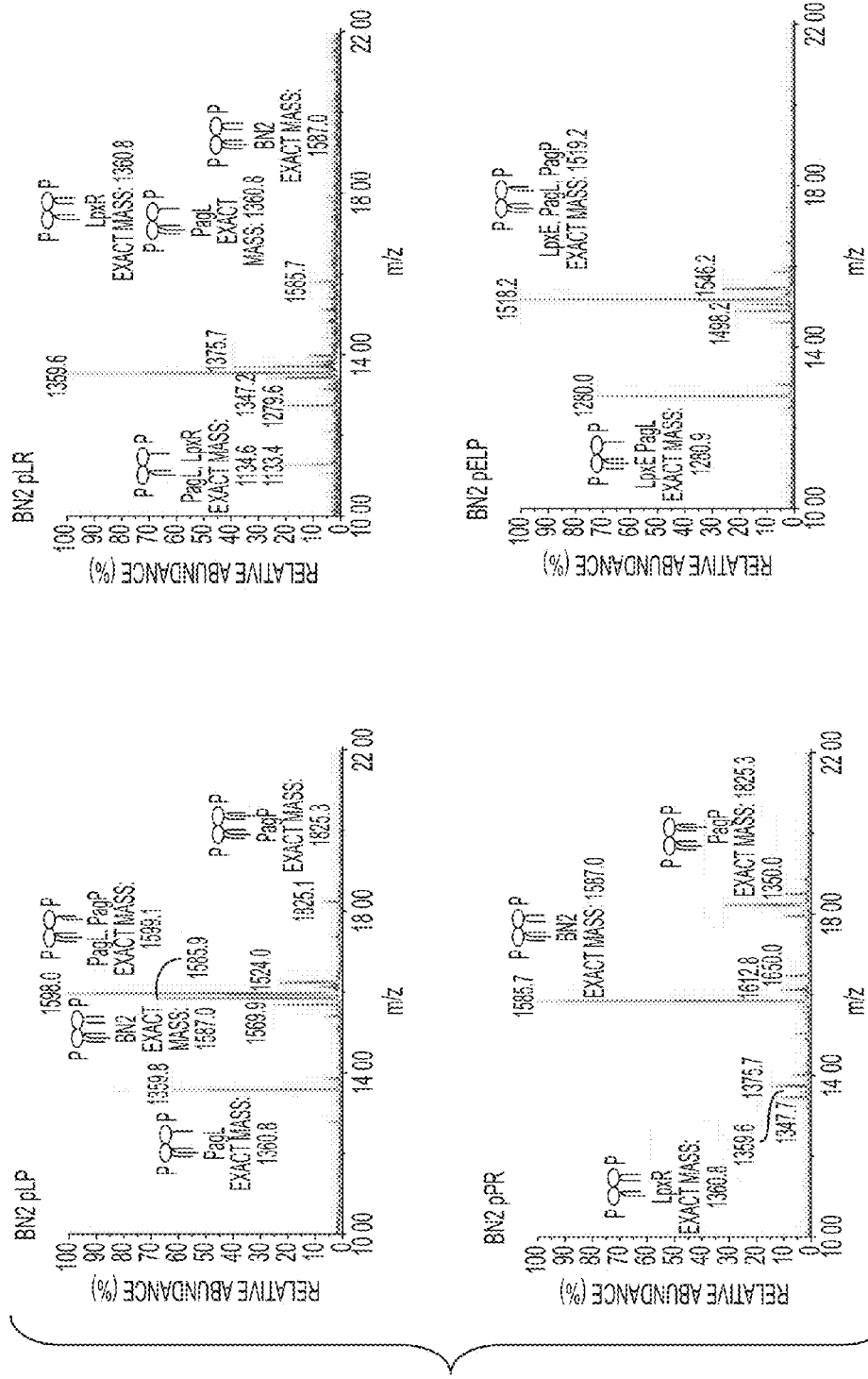
Figure 9M:
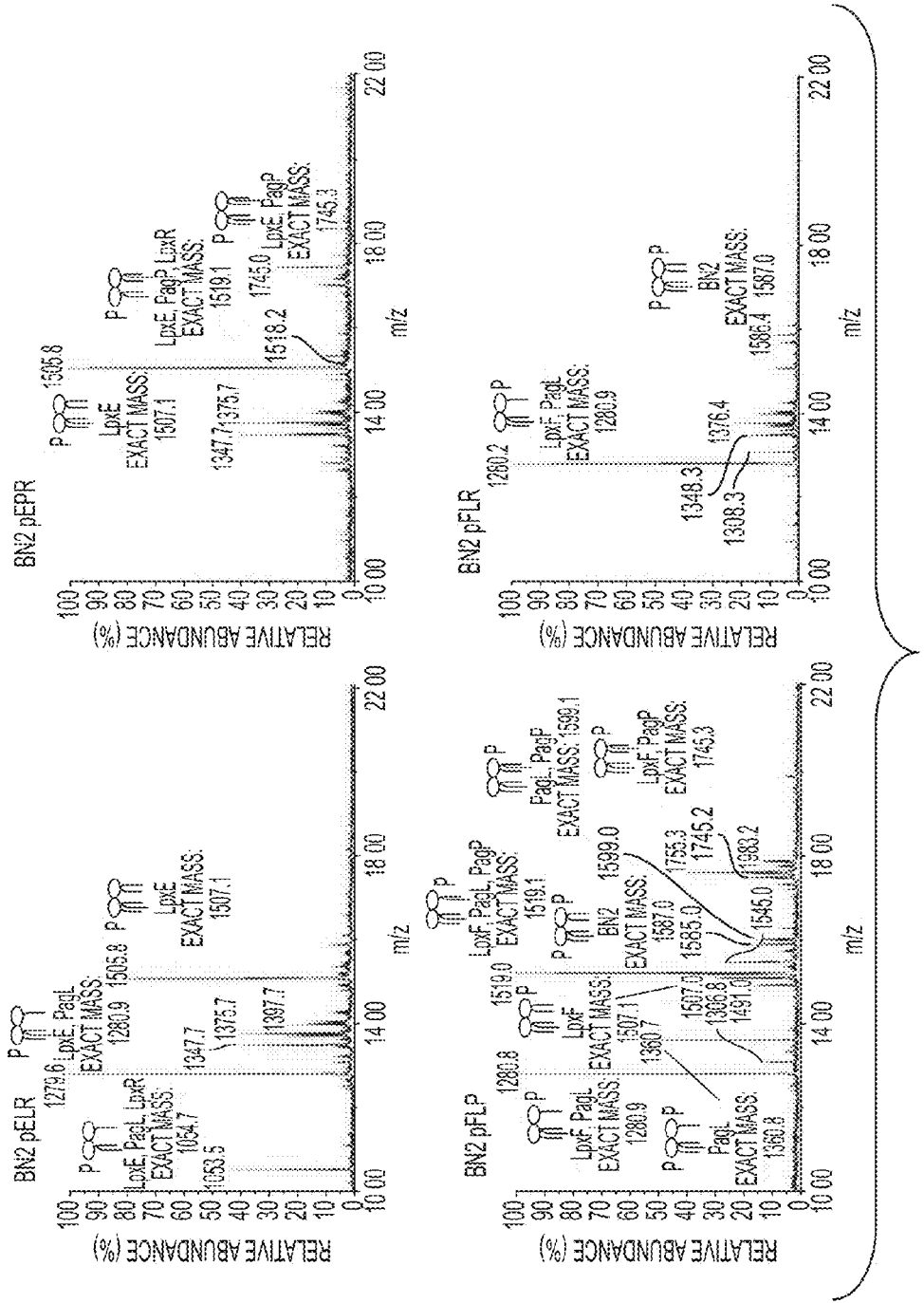
Figure 9N:
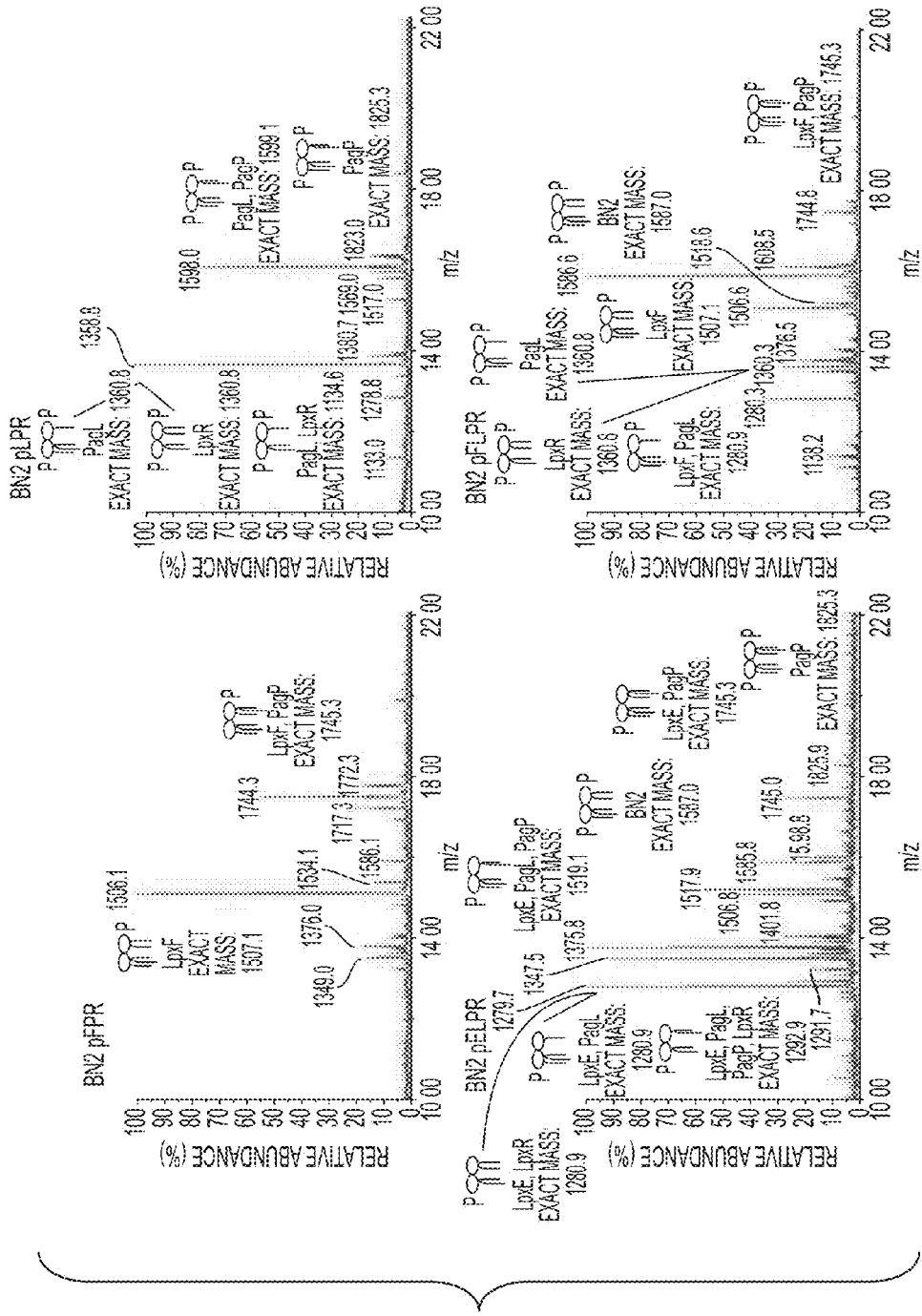
Figure 9O:
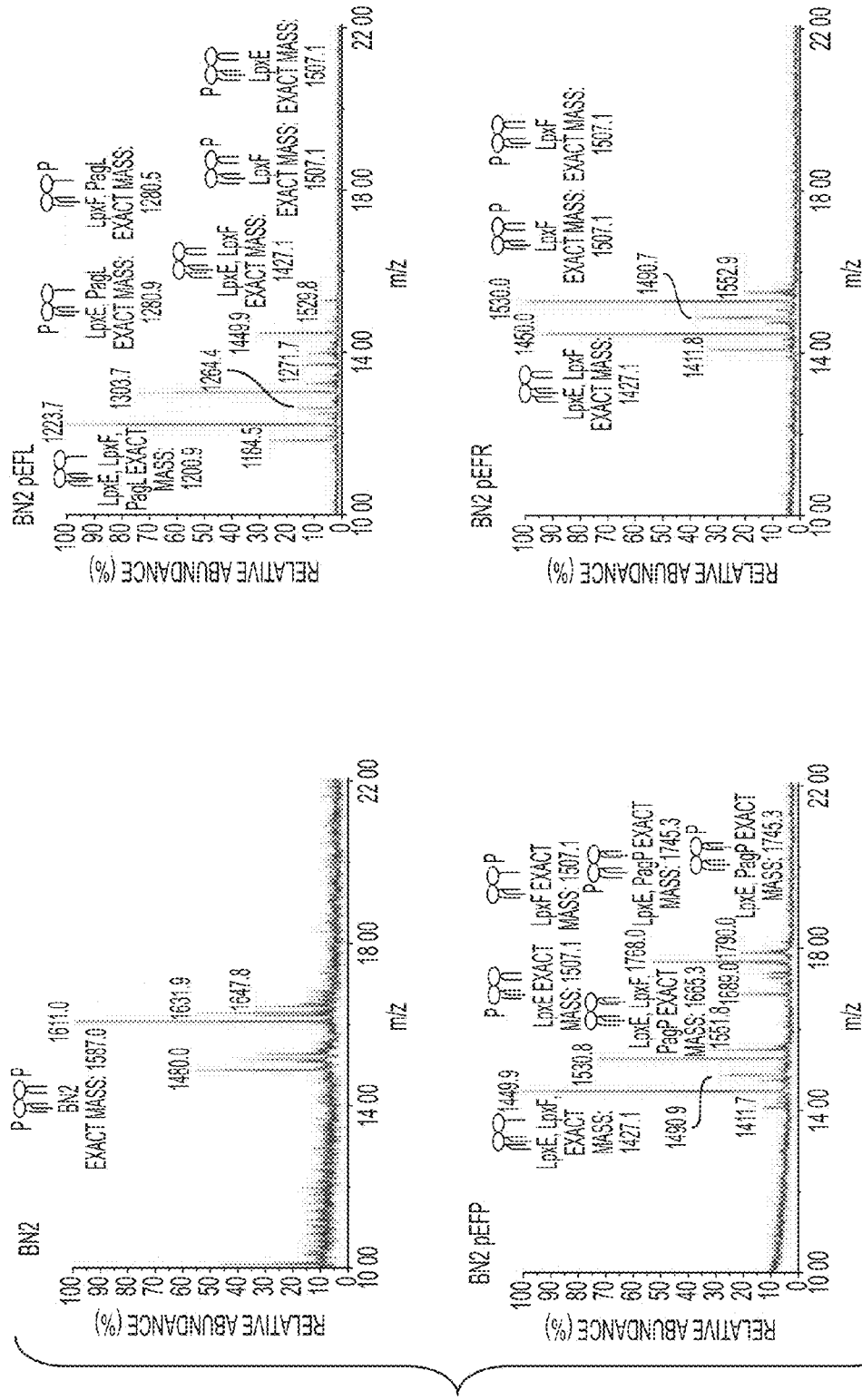
Figure 9P:
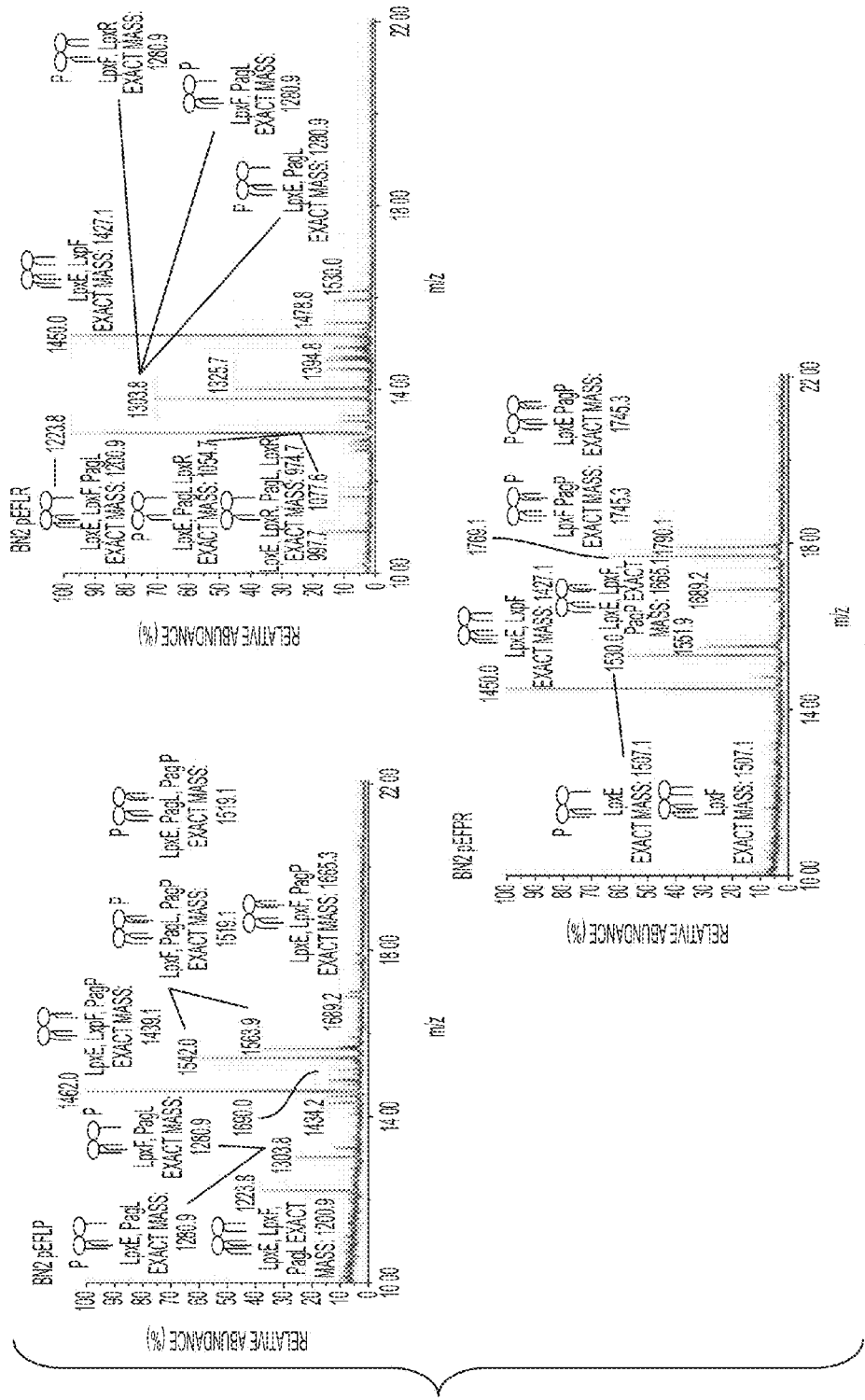

FIGS. 9A-P show mass spectra of combinatorial strains. All spectra, excluding the 3 examples presented in FIG. 3, can be found in this figure. Lipid A structures corresponding to the mass peak are depicted by cartoons next to the peak. Peak clusters at m/z ~1375 correspond to phospholipid contamination, confirmed by TLC isolation of the species. The labile 1-phosphate can be lost, resulting in a mass difference of ~80 massunits. Negative ion mode MS of BN1 and BN2 strains, respectively, confirmed the activity of the enzymes expressed in combinations. A minor species of penta-acylated lipid A can be observed in some enzyme combinations, corresponding to a peak at m/z ~1585.) Positive ion mode MS was done for all strains expressing both phosphatases, LpxE and LpxF. Positive mode often results in single or double sodium adducts on the molecules, resulting in peak masses that are ~23 or 46 mass units higher than the exact mass of each structure.

Figure 10:
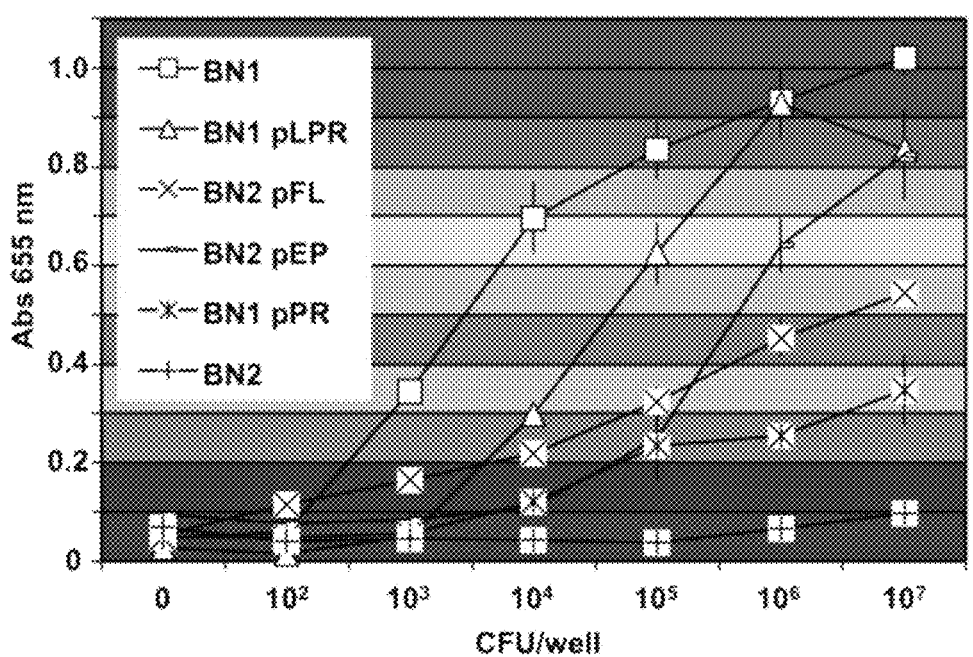
Figure 11A:
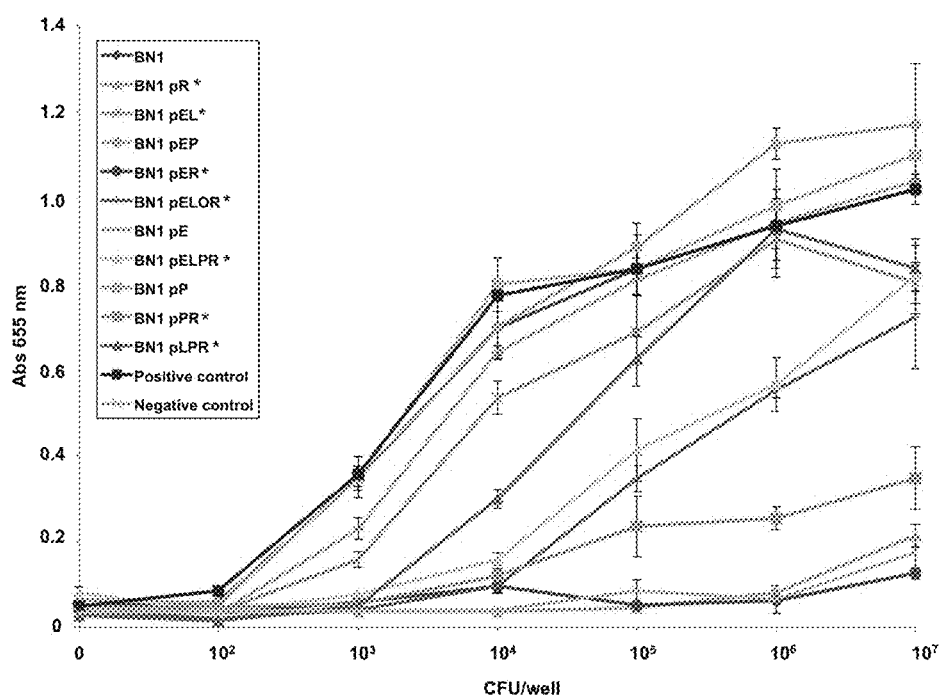
Figure 11A:
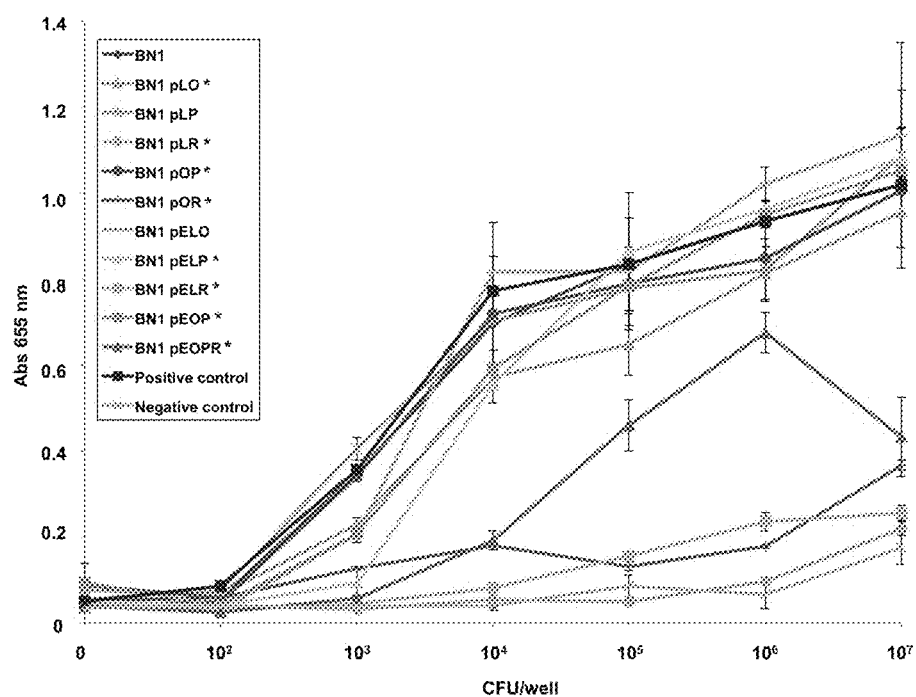
Figure 11A:
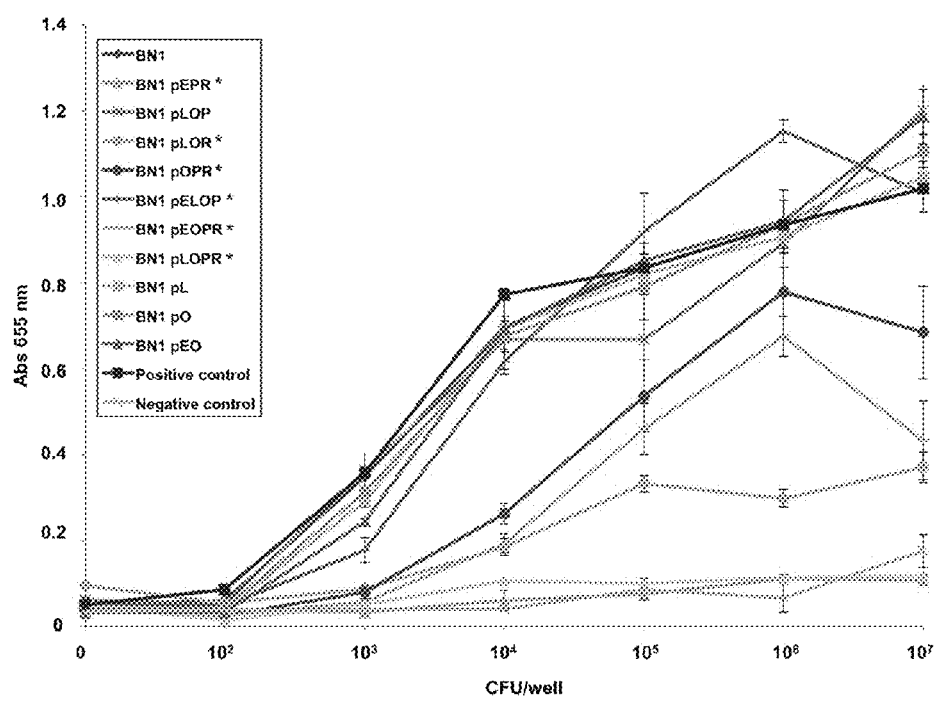
Figure 11B:
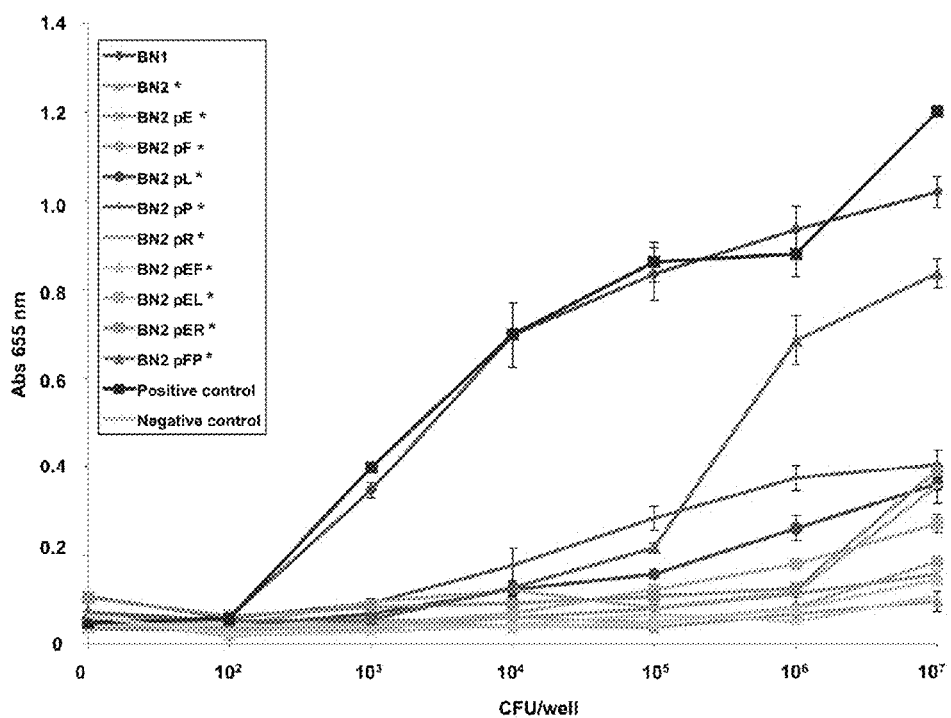
Figure 11B:
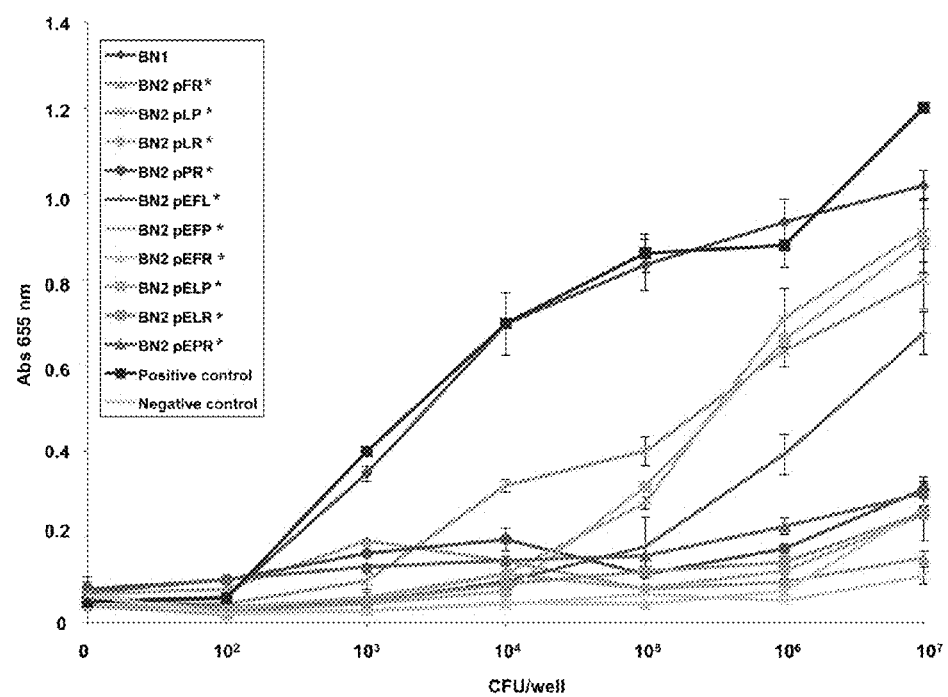
Figure 11B:
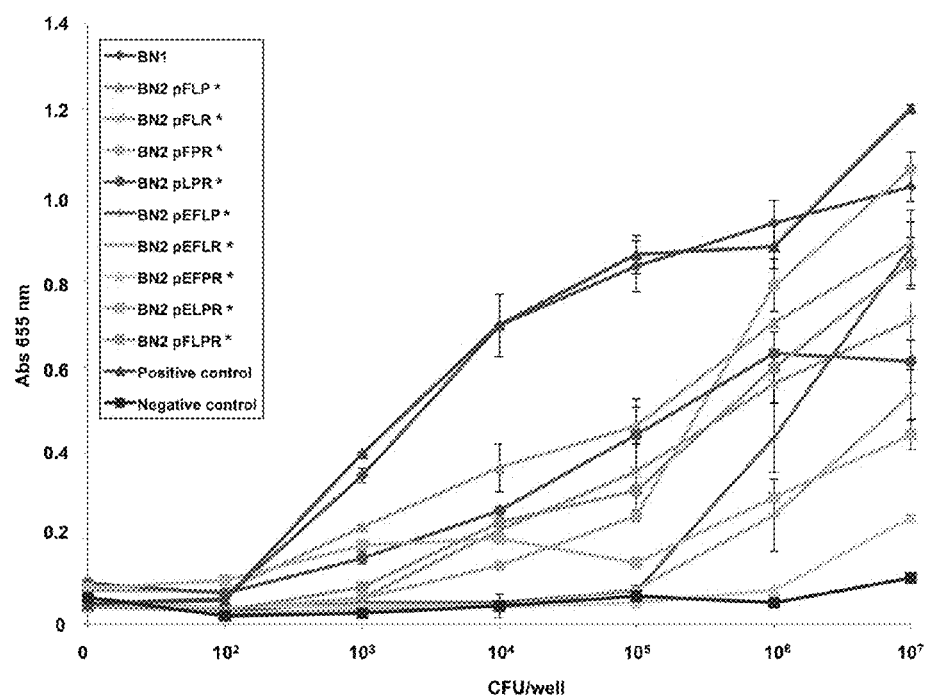

FIG. 10 shows colorimetric designations based on TLR4 stimulation by BN1. Selected samples are shown in the graph to illustrate the range of TLR4 stimulation that results from incubation of whole bacteria cells with HEK-Blue™ hTLR4 cells. Color scale is based on the stimulation curve of the BN1 sample and represents the delineations of the colorimetric scale used in FIG. 4.

FIG. 11 shows a graphical representation of TLR4 stimulation by whole bacterial cells. All TLR4 data used to generate the colorimetric scale presented in FIG. 4 is graphed here. a) TLR4 stimulation is shown of all strains in the BN1 background. These are split into three graphs due to number of samples. Samples that are significantly different from the BN1 background strain (P<0.05) are indicated by an asterisk. b) TLR4 stimulation is shown of all strains in the BN2 background, split into three graphs due to number of samples. Samples that are significantly different from the BN1 background strain (P<0.05) are indicated by an asterisk.

Figure 12:
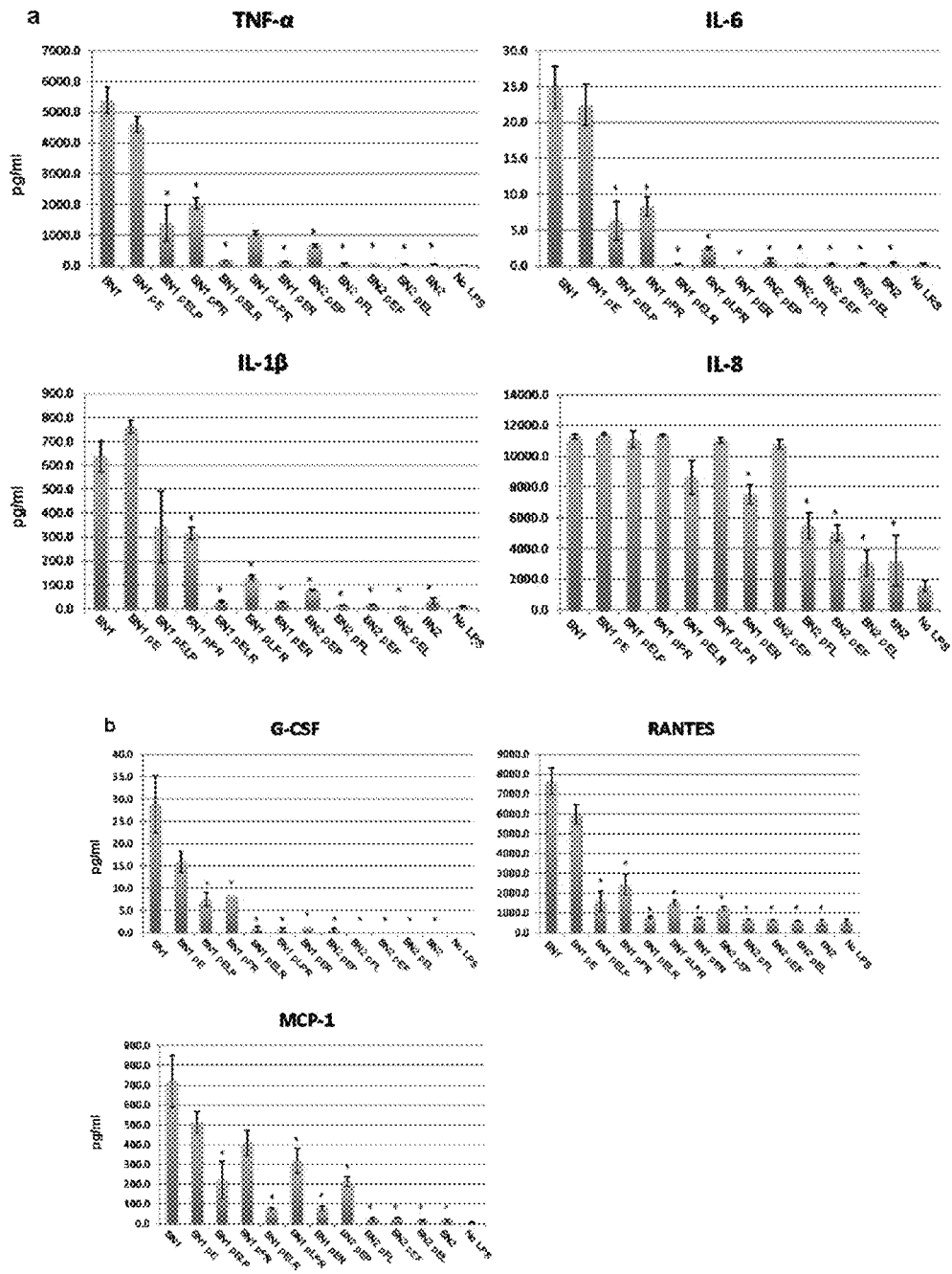

FIG. 12 shows cytokine analysis of THP-1 cells exposed to LPS. All individual cytokine data used to generate FIGS. 5b and c is presented here in picograms/ml. Asterisks indicate statistical significance with a P value <0.01 (a) Cytokines induced by the MyD88 pathway: TNF-α, IL-6, IL-1β, and IL-8. (b) Cytokines induced by the Trif pathway: G-CSF, RANTES, MCP-1. (c) P values of all samples are compared to BN1.

Figure 13:
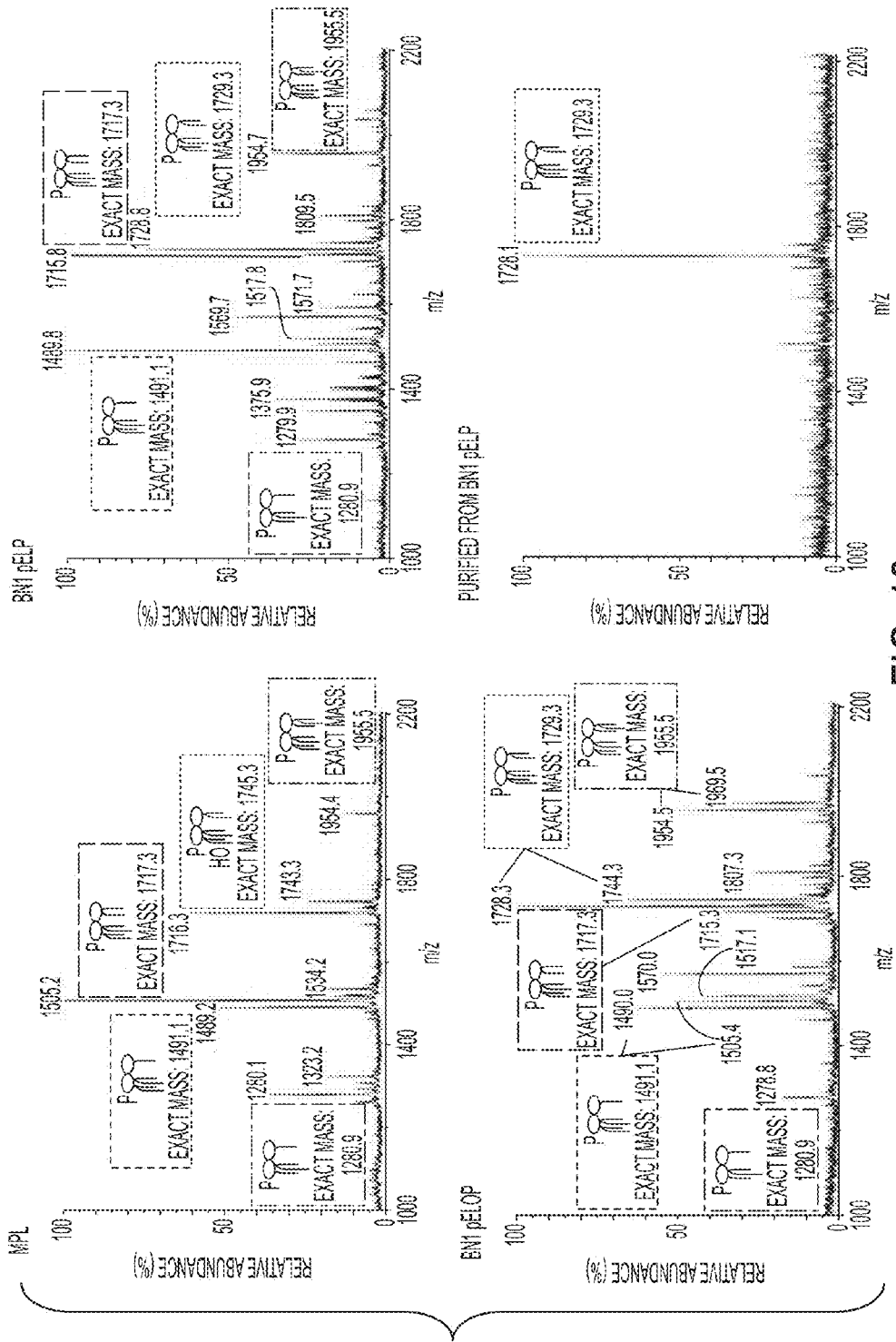

FIG. 13 shows MS of engineered strains compared to MPL™. MS data is presented of MPL from *S. minnesota* and the two strains from the library that produce similar profiles, even without additional chemical treatment or purification of individual lipid A species. Colored boxes indicate structures with the same phosphorylation and acyl chain patterns. Orange box refers to 3-O-deacyl-4'-monophosphoryl lipid A species in its hydroxylated and nonhydroxylated forms. Purified MPL from strain BN1 pELP is also shown.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

The features and advantages of the present invention will be apparent to those skilled in the art. While numerous changes may be made by those skilled in the art, such changes are within the spirit of the invention.

Description

The present disclosure generally relates to genetic engineering of bacteria. More particularly, the present disclosure relates to genetic engineering of Gram-negative bacteria expressing different species of lipid A on their surface.

The lipopolysaccharide (LPS) covering the surface of Gram-negative bacteria is a bioactive molecule with remarkable therapeutic potential. However, due to the severe inflammatory response it induces, it can be a dangerous component of vaccines and pharmaceuticals. Lipid A (endotoxin) serves as the hydrophobic anchor of LPS and is recognized by the TLR4/MD2 receptor of mammalian innate immune systems. Interestingly, Gram-negative bacteria have evolved to covalently modify their endotoxin structure, aiding in evasion of the immune response. To exploit this machinery, combinations of endotoxin modification enzymes were used to generate a library of *E. coli* strains (Table 1), each presenting unique lipid A species on its surface. Engineered bacterial cells and purified LPS from their surface stimulated a wide range of TLR4 activation, resulting in differential cytokine induction.

Utilizing lipid A modification enzymes and knowledge of lipid A/TLR4 interaction allows a library of LPS molecules exhibiting a wide range of toxicity to be constructed (FIG. 1). Taking a synthetic lipid biology and combinatorial engineering approach, the present disclosure provides for the generation of a library of 61 *E. coli* strains producing LPS molecules with unique lipid A anchors (Table 1 and FIG. 2c). Presentation of these lipids on a bacterial surface has generated LPS molecules with a broad range of effect on innate immune recognition and cytokine production. The present disclosure offers the ability to select from a range of inflammation and cytokine induction that current adjuvant options cannot provide.

Technology has long existed to purify LPS from any Gram-negative bacterium, and some of these LPS molecules may have lowered endotoxicity. However, most Gram-negatives encode lipid A modifying enzymes that are activated in various conditions and result in heterogeneous, sometimes uncharacterized lipid A species. Using diverse organisms for such a process introduces many biological factors that cannot be easily accounted for. The library of the present disclosure allows for great control over lipid A synthesis and provides lipid A structures that mimic both naturally occurring and novel lipid A structures, all within the background strains (BN1 and BN2 of the present disclosure) that have been generated to synthesize homogeneous, unmodified lipid A. Combinatorial strains of the library of the present disclosure were generated by transformation of BN1 and BN2 with a pQLinkN plasmid expressing combinations of the 6 lipid A modifying enzymes. BN1 and BN2 were generated by modification of *E. coli* K12 strain W3110. Each enzyme is abbreviated by its final letter and ordered alphabetically in the plasmid name, for example, LpxE is abbreviated E, LpxF is F, LpxR is R, PagP is P, PagL is L, and LpxO is O.

In certain embodiments, the present disclosure also provides engineered strains that are non-toxic. For example, BN2, BN2 pEF, BN2 pF, BN2 pE, BN2 pFR, BN2 pEFR, BN2 pEFPR, BN2 pLR, BN2 pEL, BN2 pELR, BN1 pER, BN1 pEPR, BN1 pLOPR, BN1 pR, BN1 pLR, BN1 pELR in whole cell form contain non-toxic LPS. In certain other embodiments, purified LPS from these strains may also be non-toxic. For example, non-toxic purified LPS includes, but is not limited to, LPS purified from BN2, BN2 pEL, and BN2 pEF.

These strains will improve the use of *E. coli* in whole cell form (in addition to purifying the LPS they produce) when LPS toxicity has been a problem in the past. The present disclosure illustrates that the alteration of the lipid A portion of LPS is sufficient to affect the overall response, regardless of other cell surface bacterial mediators of inflammation (e.g. flagellar proteins, lipoproteins). Accordingly, the library of the present disclosure provides specifically modified strains as a template that may be used, for example, for basic research into bacterial membranes, membrane proteins, and lipid A modification enzymes.

In one embodiment, the Gram-negative bacteria used according to the present disclosure are *Escherichia coli* (*E. coli*) that have been engineered to synthesize homogeneous, unmodified lipid A. However, other Gram-negative bacteria may be used that have been engineered to synthesize homogeneous, unmodified lipid A. The surface of almost all Gram-negative bacteria is composed of LPS, but some species that synthesize unique LPS structures are fastidious and difficult to work with in a laboratory setting. *E. coli*, on the other hand, has long been developed as a laboratory system and is very well-characterized and easy to grow. The *E. coli* strains of the present disclosure have the benefit of simple growth requirements yet can synthesize many complex and unique LPS structures.

*E. coli* is ideal for inexpensive mass production of molecules such as DNA and protein, but LPS is a major contaminant in such pharmaceutical preparations. To purify samples within the safe clinical grade limits, many purification methods have been developed. Unfortunately, the variety of biotechnological applications utilizing *E. coli* makes it difficult to establish general methodologies for removal of LPS. Additionally, these steps often sacrifice yield for purity, add hours to sample preparation, and require large-scale, expensive disposable supplies. The present disclosure provides, in certain embodiments, for the use of engineered *E. coli* strains with a decreased threat of endotoxic impurity so as to eliminate the need for difficult purification methods. The surface structure of the *E. coli* strains in the library of the present disclosure is modified by proteins encoded on a plasmid. The genes encoding the proteins are selected from lpxE, lpxF, lpxO, lpxR, pagL, and pagP. The proteins encoded on the plasmid are generally lipid A modification enzymes.

The plasmids may be lost from the bacterium during long-term growth inside a host. Such bacterial growth can be necessary in whole cell vaccines. However, if plasmid expression is not induced and the plasmid is lost, the surface structure of the cells will revert to a wild type, unmodified form. In one embodiment, this disadvantage can be overcome by genetically engineering the genes encoding each enzyme into the chromosome of the strain to remove dependence on plasmid maintenance. The limitation caused by plasmid expression only occurs when whole cells need to be maintained for many generations in vivo, and is not a problem when the cells are used in the laboratory or when LPS is purified from the strains.

The structural nature of E. coli lipid A, with six acyl chains and two phosphate groups, is critical for complete activation of human TLR4/MD-2. Many bacteria have evolved enzymes that modify lipid A, aiding in evasion of the immune system. These enzymes have various functions, such as modifying acyl chain number, removing phosphate groups, or adding polar functional groups, which leads to alteration of the host immune response. In addition to lowered TLR4 stimulation, structural variation of lipid A can stimulate select TLR4 pathways through the recruitment of different sets of adaptor proteins. Exploiting lipid A modifications to obtain differential TLR4 stimulation could allow the selection of specific cytokine production for many applications, such as improved vaccines, detoxified protein expression strains, anti-sepsis drugs, and gene therapy strains.

The library of the present disclosure provides 61 E. coli strains that could be utilized as whole cells, LPS, or lipid A suitable for numerous applications. For example, the library of the present disclosure can be used in atoxic bacterial expression systems (protein purification, for example), bacterial strains for gene therapy, cancer vaccines, and attenuated whole bacterial vaccines. The library of LPS/lipid A molecules of the present disclosure can be used, for example, as adjuvants, antisepsis drugs, and for cancer treatments. The library of the present disclosure also provides a versatile tool and illustrates the utility of E. coli for production of modified lipid A molecules. The ability to select an optimal inflammatory response to cells, LPS, and lipid A could be beneficial to many applications, including, but not limited to, protein purification strains, gene therapy strains, vaccine adjuvants, and anti-sepsis drugs.

The high inflammatory response to E. coli is an obstacle to gene therapy. Gene therapy strains are engineered to lyse upon phagocytosis and transfer a plasmid with mammalian expression machinery to the host. For this purpose, a strain producing penta-acylated lipid A was generated to reduce the proinflammatory activity (Grilo-Courvalin et al., 2011), but an intermediate immune response might offer an elegant balance between high phagocytosis and lowered endotoxicity. Gene therapy strains can also be engineered to colonize tumors and express tumor antigens to initiate an oncolytic response. This reaction is partly due to the lipid A/TLR4 response and the production of tumor necrosis factor (Rockwell et al., 2009). In fact, lipid A immunogenicity has been shown to be responsible for tumor regression in various models and tissue types (Carswell et al., 1975). The library of the present disclosure may allow for the selection of a strain of E. coli which will produce an intermediate immune response suitable for use in gene therapy applications.

The library of the present disclosure is also designed to provide means for further exploration of the potential of LPS. These strains were constructed using single plasmid-based combinatorial expression of lipid A modification enzymes and the resultant lipid A phenotypes were confirmed by both TLC and MS. Bioactivity of engineered cells and purified LPS was explored through TLR4 and cytokine assays, revealing significant variation between strains. Engineered LPS can be utilized in a number of ways including, but not limited to, as (i) the major immunogenic surface component of whole bacteria, (ii) to create a purified LPS molecule, or (iii) to create free lipid A molecules following LPS hydrolysis. These components can be used for diverse applications, including but not limited to, the design of improved vaccines, anti-sepsis drugs, cancer therapeutics, gene therapy and atoxic bacterial expression systems.

One LPS derivative with reduced toxicity, termed MPL™, has been approved to supplement an adjuvant system in vaccines worldwide. MPL™ is actually a mixture of lipid A species from Salmonella minnesota R595 that have been chemically detoxified. The primary lipid A species present in MPL™ is 3-O-deacyl-4'-monophosphoryl lipid A (FIG. 7). MPL™ induces a cytokine profile that is less inflammatory than LPS, yet it remains an effective adjuvant. To facilitate the biological production of MPL™, E. coli strains that produce 4'-monophosphoryl-lipid A have been developed (Chen et al., 2011; Kawasaki et al., 2004); however, the acyl chain arrangement in lipid A from these strains varies structurally from the significant 3-O-deacyl-4'-monophosphoryl lipid A species in MPL™. An E. coli strain producing MPL™ has not been previously reported. The library of the present disclosure includes E. coli strains producing lipid A species of MPL™ (BN1 pELP and BN1 pELOP). In certain embodiments, the present disclosure provides a method for preparing MPL™. Generally, preparation of MPL™ requires purification of the lipid A moiety followed by chemical treatment, involving successive acid and base hydrolysis. Generally, if a particular species of lipid A is desired from a mixture of lipid A that is isolated from LPS, liquid chromatography can be performed to isolate the desired species. Strains in the library of the present disclosure, BN1 pELP and BN1 pELOP, synthesize MPL™ lipid A structure independently, eliminating the need for acid and base treatment. Purification of 3-O-deacyl-4'-monophosphoryl lipid A produced by strain BN1 pELP was performed by reverse-phase chromatography (FIG. 13) with ~0.4-0.6 mg of the target lipid obtained per liter of culture. Based upon TLC analysis, approximately $\frac{1}{3}^{rd}$ of the lipid A synthesized is 3-O-deacyl-4'-monophosphoryl lipid A. Assuming there are $10^9$ CFU/ml of bacteria at an $OD_{600}$ of 1.0 and ~$10^6$ lipid A molecules per cell (Raetz 2007), the maximum yield of the target lipid would be ~1 mg/L of culture.

To satisfy both pharmaceutical and therapeutic needs, in one embodiment, lipid A of the library of the present disclosure would be made available in a spectrum of endotoxicity. For example, minimal endotoxicity is desirable for bacterial expression systems, whereas modest immunogenicity is more suitable for safe use in vaccines.

In the library of the present disclosure, co-expressed lipid A modification enzymes produced a range of TLR4 responses and cytokine profiles. Some enzyme combinations confirmed previously untested assumptions. Strains containing LpxR, for example, showed greatly reduced TLR4 stimulation. However, other combinations could not have been predicted, like BN2 pFL, which is tetra-acylated and 4'-dephosphorylated yet consistently shows higher TLR4 stimulation by both whole bacterial cells and LPS than its penta-acylated, bis-phosphorylated parent (FIG. 4). The ability to use a strain with essentially no endotoxicity and incrementally increase the level, as in BN2 pFL, could provide a safe alternative to detoxifying an immunogenic strain that requires extensive quality control to avoid dangerous endotoxin contamination.

Figure 3A:
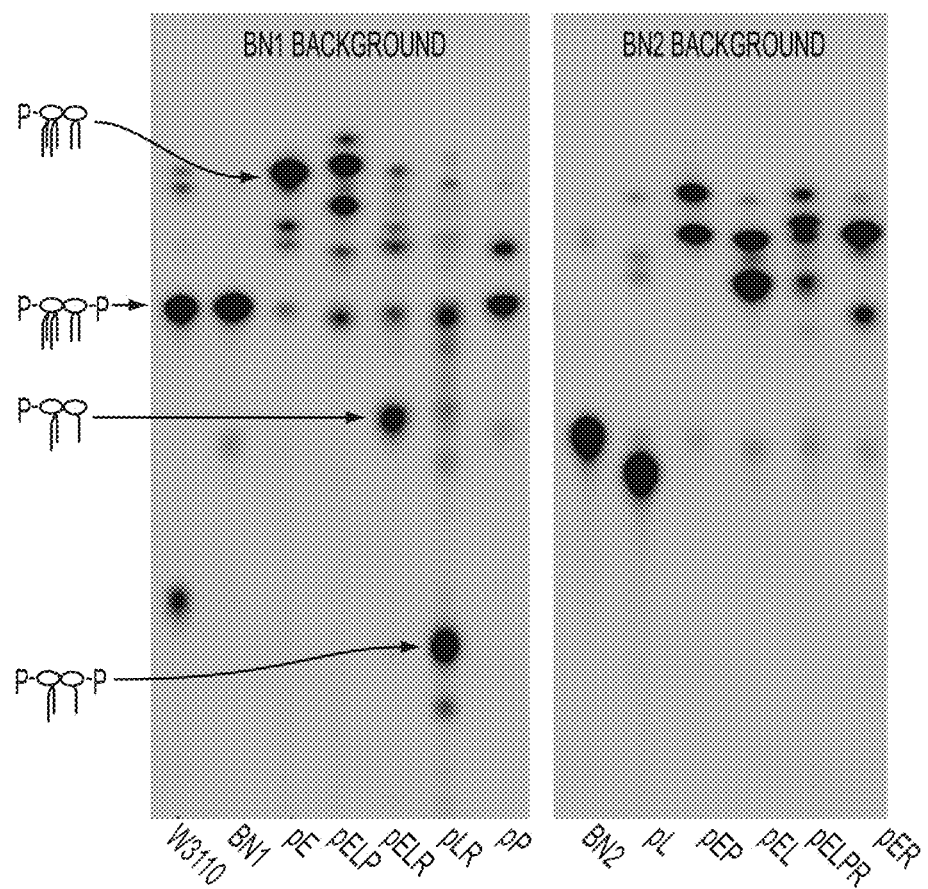
Figure 3B:
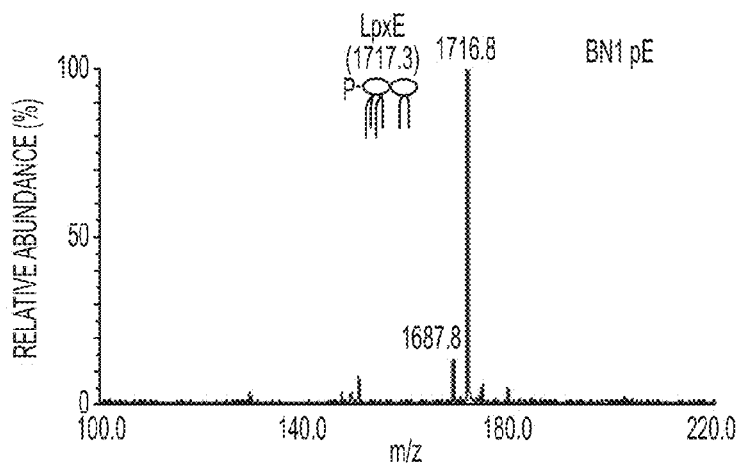
Figure 3C:
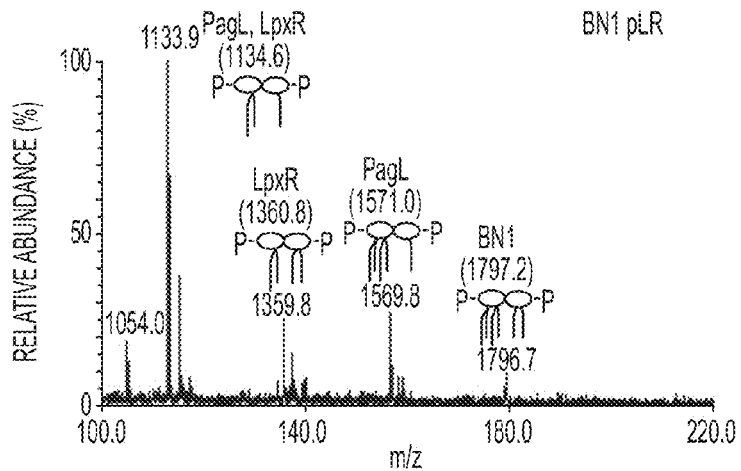

Some combinations, such as the greatly modified monophosphorylated, tri-acylated lipid A of strain BN1 pLR, show that E. coli tolerates severe changes in lipid A without major growth defects (FIG. 3c).

In certain embodiments, purified LPS and lipid A engineered according the present disclosure may be used in the treatment of cancer. One major hindrance to the use of purified LPS and lipid A in cancer treatments is tolerance. Tolerance develops even after one treatment, with downregulation of the immune response to LPS. Although this is detrimental to cancer treatment, it is a beneficial development for protection against sepsis for immunosuppressed patients. Some lipid A analogs, such as MPL™, induce less tolerance than LPS. Direct comparison between lipid A structures could provide insight into the mechanism of tolerance, potentially decrease tolerance for tumor regression treatments, or increase it for protection against endotoxic shock.

In another embodiment, the present disclosure may provide for improved delivery of vaccines. For example, MPL™ is a derivative from LPS that is also less inflammatory, but it is insoluble and must be adsorbed to other adjuvants for mechanical delivery. The engineered LPS molecules of the present disclosure contain both lipid (e.g. MPL™) and carbohydrate moieties increasing solubility.

In other embodiments, the present disclosure provides improved vaccine adjuvants generated from the library of the present disclosure. Tolerance has excluded MPL™ from cancer treatments but has not eliminated it from attention as a cancer vaccine adjuvant. In fact, although many synthetic analogs are being investigated, MPL™ is the only lipid A to date that has been tested in human clinical cancer vaccine trials. Considering the evidence that TLR4 signaling can be biased to produce certain types of responses, other lipid A structures should be explored as well. Few studies have directly compared the effects of other lipid A structures to MPL™ and to LPS. However, lipid A is insoluble and requires adsorption onto other adjuvants to enable delivery, so a modified LPS of the present disclosure could offer more options for a soluble molecule with the lowered endotoxicity of MPL™. The combinatorial approach of the present disclosure allows investigation into the potential for custom induction of immune responses.

Targeting a particular TLR4 response by administering engineered LPS could offer better vaccine adjuvants. However, predominant adjuvants (e.g. aluminum salts) do not sufficiently induce antibacterial and antiviral TH1 immune responses. LPS does elicit a strong TH1 response, but the molecule is too inflammatory for safe use. The engineering of modified LPS molecules according to the present disclosure could also greatly impact subunit vaccine development. In cancer vaccines and other subunit vaccines, pathogen specific antigens are often too weakly immunogenic to be effective and require an adjuvant to boost the antigen-specific immune response.

In another embodiment, the library of the present disclosure may provide for long lasting, specific immunity in vaccines. For example, in certain embodiments, E. coli strains with modified LPS have been engineered that induce a lower immune response but are still able to elicit a strong TH1 response. This offers an alternative to known adjuvants, such as aluminum salts that do not sufficiently stimulate a TH1 response and wild type LPS that is too inflammatory. The present disclosure provides more options to control the level of boost that each subunit needs to elicit the appropriate TH1 response. Thus, insufficient immunogenicity can be enhanced by LPS adjuvants, and those antigens with intermediate immune responses can be slightly elevated by selecting LPS molecules from the library of the present disclosure.

It remains to be tested whether some lipid A species in the library possess antagonistic properties. As antisepsis drugs, they could reduce the high number of deaths in intensive care units due to septic shock. Additionally, supplementation with antagonist species of LPS has been shown to downregulate a hyperinflammatory response to some antigens or whole cell vaccines (Peri et al., 2011; Geurtsen et al., 2008). Some of these antagonists could also treat neuropathic pain, which has been linked to TLR4 stimulation.

TABLE 1

The Library

|   | Strain Generated | Genotype or description |
|---|---|---|
| 1 | BN1 | W3110 ΔeptA, ΔlpxT, ΔpagP |
| 2 | BN2 | BN1 ΔlpxM::kan |
| 3 | BN1 pE | BN1 pQLinkN containing lpxE |
| 4 | BN1 pL | BN1 pQLinkN containing pagL |
| 5 | BN1 pO | BN1 pQLinkN containing lpxO |
| 6 | BN1 pP | BN1 pQLinkN containing pagP |
| 7 | BN1 pR | BN1 pQLinkN containing lpxR |
| 8 | BN1 pEL | BN1 pQLinkN containing lpxE, pagL |
| 9 | BN1 pEO | BN1 pQLinkN containing lpxE, lpxO |
| 10 | BN1 pEP | BN1 pQLinkN containing lpxE, pagP |
| 11 | BN1 pER | BN1 pQLinkN containing lpxE, lpxR |
| 12 | BN1 pLO | BN1 pQLinkN containing pagL, lpxO |
| 13 | BN1 pLP | BN1 pQLinkN containing pagL, pagP |
| 14 | BN1 pLR | BN1 pQLinkN containing pagL, lpxR |
| 15 | BN1 pOP | BN1 pQLinkN containing lpxO, pagP |
| 16 | BN1 pOR | BN1 pQLinkN containing lpxO, lpxR |
| 17 | BN1 pPR | BN1 pQLinkN containing pagP, lpxR |
| 18 | BN1 pELO | BN1 pQLinkN containing lpxE, pagL, lpxO |
| 19 | BN1 pELP | BN1 pQLinkN containing lpxE, pagL, pagP |
| 20 | BN1 pELR | BN1 pQLinkN containing lpxE, pagL, lpxR |
| 21 | BN1 pEOP | BN1 pQLinkN containing lpxE, lpxO, pagP |
| 22 | BN1 pEPR | BN1 pQLinkN containing lpxE, pagP, lpxR |
| 23 | BN1 pLOP | BN1 pQLinkN containing pagL, lpxO, pagP |
| 24 | BN1 pLOR | BN1 pQLinkN containing pagL, lpxO, lpxR |
| 25 | BN1 pLPR | BN1 pQLinkN containing pagL, pagP, lpxR |
| 26 | BN1 pOPR | BN1 pQLinkN containing lpxO, pagP, lpxR |
| 27 | BN1 pELOP | BN1 pQLinkN containing lpxE. pagL, lpxO, pagP |
| 28 | BN1 pELOR | BN1 pQLinkN containing lpxE. pagL, lpxO, lpxR |
| 29 | BN1 pELPR | BN1 pQLinkN containing lpxE, pagL, pagP, lpxR |
| 30 | BN1 pEOPR | BN1 pQLinkN containing lpxE, lpxO, pagP, lpxR |
| 31 | BN1 pLOPR | BN1 pQLinkN containing pagL, lpxO, pagP, lpxR |
| 32 | BN2 pE | BN2 pQLinkN containing lpxE |
| 33 | BN2 pF | BN2 pQLinkN containing lpxF |
| 34 | BN2 pL | BN2 pQLinkN containing pagL |
| 35 | BN2 pP | BN2 pQLinkN containing pagP |
| 36 | BN2 pR | BN2 pQLinkN containing lpxR |
| 37 | BN2 pEF | BN2 pQLinkN containing lpxE, lpxF |
| 38 | BN2 pEL | BN2 pQLinkN containing lpxE, pagL |
| 39 | BN2 pEP | BN2 pQLinkN containing lpxE, pagP |
| 40 | BN2 pER | BN2 pQLinkN containing lpxE, lpxR |
| 41 | BN2 pFL | BN2 pQLinkN containing lpxF, pagL |
| 42 | BN2 pFP | BN2 pQLinkN containing lpxF, pagP |
| 43 | BN2 pFR | BN2 pQLinkN containing lpxF. lpxR |
| 44 | BN2 pLP | BN2 pQLinkN containing pagL, pagP |
| 45 | BN2 pLR | BN2 pQLinkN containing pagL, lpxR |
| 46 | BN2 pPR | BN2 pQLinkN containing pagP, lpxR |
| 47 | BN2 pEFL | BN2 pQLinkN containing lpxE, lpxF, pagL |
| 48 | BN2 pEFP | BN2 pQLinkN containing lpxE, lpxF, pagP |
| 49 | BN2 pEFR | BN2 pQLinkN containing lpxE, lpxF, lpxR |
| 50 | BN2 pELP | BN2 pQLinkN containing lpxE, pagL, pagP |
| 51 | BN2 pELR | BN2 pQLinkN containing lpxE, pagL, lpxR |
| 52 | BN2 pEPR | BN2 pQLinkN containing lpxE, pagP, lpxR |
| 53 | BN2 pFLP | BN2 pQLinkN containing lpxR, pagL, pagP |
| 54 | BN2 pFLR | BN2 pQLinkN containing lpxF, pagL, lpxR |
| 55 | BN2 pFPR | BN2 pQLinkN containing lpxF, pagP, lpxR |

TABLE 1-continued

The Library

| Strain Generated | | Genotype or description |
|---|---|---|
| 56 | BN2 pLPR | BN2 pQLinkN containing pagL, pagP, lpxR |
| 57 | BN2 pELPR | BN2 pQLinkN containing lpxE, pagL, pagP, lpxR |
| 58 | BN2 pEFLP | BN2 pQLinkN containing lpxE, lpxF, pagL, pagP |
| 59 | BN2 pEFLR | BN2 pQLinkN containing lpxE. lpxF, pagL, lpxR |
| 60 | BN2 pEFPR | BN2 pQLinkN containing lpxE, lpxF, pagP, lpxR |
| 61 | BN2 pFLPR | BN2 pQLinkN containing lpxF. pagL, pagP, lpxR |

To facilitate a better understanding of the present invention, the following examples of certain aspects of some embodiments are given. In no way should the following examples be read to limit, or define, the entire scope of the invention.

EXAMPLES

Construction of Mutant Strains

Table 2 shows the bacterial strains and plasmids used in this study. All gene deletions were performed by P1 vir phage transduction using Keio collection mutants as donors, as previously described (Herrera et al., 2010, Baba et al., 2006). Antibiotic cassettes were removed as described previously (Datsenko et al, 2000). BN1 was generated from BN0, an lpxT and eptA double mutant. The LpxT enzyme functions to add a third phosphate to lipid A, and when mutated the lipid A should be bis-phosphorylated. However, LpxT inhibition activates EptA, which adds a phosphoethanolamine to the 1-position of lipid A. Mutation of lpxT and eptA activates PagP to palmitoylate the 2-acyl chain of lipid A, so the pagP gene was also deleted. PagP was used in plasmids to generate the library of the present disclosure, so its mutation prevented confounding modifications to the lipid A. Deletion of all three genes resulted in a strain that makes >95% of the prototypical, hexa-acylated bis-phosphorylated lipid A species (FIG. 7). To double the potential lipid A profiles that could be produced from one set of enzymes, BN2 was generated by removal of the Kan$^R$ cassette and deletion of lpxM from BN1. LpxM is responsible for adding a myristate to the 3' acyl chain on the glucosamine disaccharide of lipid A. Strains were confirmed by PCR using primers flanking each gene, $^{32}$P radiolabeling, and MS (Table 3, data not shown, FIG. 7) (Baba et al., 2006).

TABLE 2

Bacterial strains and plasmids used in this study.

| Strain or plasmid | Genotype or description | Source or reference |
|---|---|---|
| Strains | | |
| W3110 | Wild type, F⁻ 1⁻ rph-1 INV(rrnD, rrnE)1 rph-1 | E. coli Genetic Stock center (Yale) |
| MLK1067 | W3110 lpxM::Ωcam | Karow et al., 1992 |
| CMR300 | W3110 (kdtA::kan) pWMsbA | Reynolds et al. 2009 |
| BN0 | W3110 ΔeptA::cam, ΔlpxT | This work |
| BN1 | BN0 ΔpagP | This work |
| BN2 | BN1 ΔlpxM::kan | This work |

TABLE 2-continued

Bacterial strains and plasmids used in this study.

| Strain or plasmid | Genotype or description | Source or reference |
|---|---|---|
| Plasmids | | |
| pQLinkN | Vector containing a tac promotor, Amp$^r$ | Addgene plasmid 13670 |
| pE | pQLinkN containing lpxE | This work |
| pF | pQLinkN containing lpxF | This work |
| pL | pQLinkN containing pagL | This work |
| pO | pQLinkN containing lpxO | This work |
| pP | pQLinkN containing pagP | This work |
| pR | pQLinkN containing lpxR | This work |
| pEL | pQLinkN containing lpxE, pagL | This work |
| pEO | pQLinkN containing lpxE, lpxO | This work |
| pEP | pQLinkN containing lpxE, pagP | This work |
| pER | pQLinkN containing lpxE, lpxR | This work |
| pLO | pQLinkN containing pagL, lpxO | This work |
| pLP | pQLinkN containing pagL, pagP | This work |
| pLR | pQLinkN containing pagL, lpxR | This work |
| pOP | pQLinkN containing lpxO, pagP | This work |
| pOR | pQLinkN containing lpxO, lpxR | This work |
| pPR | pQLinkN containing pagP, lpxR | This work |
| pELO | pQLinkN containing lpxE, pagL, lpxO | This work |
| pELP | pQLinkN containing lpxE, pagL, pagP | This work |
| pELR | pQLinkN containing lpxE, pagL, lpxR | This work |
| pEOP | pQLinkN containing lpxE, lpxO, pagP | This work |
| pEPR | pQLinkN containing lpxE, pagP, lpxR | This work |
| pLOP | pQLinkN containing pagL, lpxO, pagP | This work |
| pLOR | pQLinkN containing pagL, lpxO, lpxR | This work |
| pLPR | pQLinkN containing pagL, pagP, lpxR | This work |
| pOPR | pQLinkN containing lpxO, pagP, lpxR | This work |
| pELOP | pQLinkN containing lpxE. pagL, lpxO, pagP | This work |
| pELOR | pQLinkN containing lpxE. pagL, lpxO, lpxR | This work |
| pELPR | pQLinkN containing lpxE, pagL, pagP, lpxR | This work |
| pEOPR | pQLinkN containing lpxE, lpxO, pagP, lpxR | This work |
| pLOPR | pQLinkN containing pagL, lpxO, pagP, lpxR | This work |
| pEF | pQLinkN containing lpxE, lpxF | This work |
| pFL | pQLinkN containing lpxF, pagL | This work |
| pFP | pQLinkN containing lpxF, pagP | This work |
| pFR | pQLinkN containing lpxF. lpxR | This work |
| pEFL | pQLinkN containing lpxE, lpxF, pagL | This work |
| pEFP | pQLinkN containing lpxE, lpxF, pagP | This work |
| pEFR | pQLinkN containing lpxE, lpxF, lpxR | This work |
| pFLP | pQLinkN containing lpxR, pagL, pagP | This work |
| pFLR | pQLinkN containing lpxF, pagL, lpxR | This work |
| pFPR | pQLinkN containing lpxF, pagP, lpxR | This work |
| pEFLP | pQLinkN containing lpxE. lpxF, pagL, pagP | This work |
| pEFLR | pQLinkN containing lpxE. lpxF, pagL, lpxR | This work |
| pEFPR | pQLinkN containing lpxE, lpxF, pagP, lpxR | This work |
| pFLPR | pQLinkN containing lpxF. pagL, pagP, lpxR | This work |

TABLE 3

Primers used in this study.

| Primer name | Primer sequence | | |
|---|---|---|---|
| LpxEBamHIfor | 5'-GCGGATCCATGCTCAAACAGACATTA-3' | SEQ ID NO: | 1 |
| LpxEBamHIrev | 5'-GCGCGGCCGCCTAAATAATCTCTCTATT-3' | SEQ ID NO: | 2 |
| LpxFBamHIfor | 5'-GCGGATCCTTGGCAAGATTTCATATC-3' | SEQ ID NO: | 3 |
| LpxFBamHIrev | 5'-GCGCGGCCGCTCAATATTCTTTTTTACG-3' | SEQ ID NO: | 4 |
| PagLBamHIfor | 5'-GCGGATCCATGTATATGAAGAGAATA-3' | SEQ ID NO: | 5 |
| PagLBamHIrev | 5'-GCGCGGCCGCTCAGAAATTATAACTAAT-3' | SEQ ID NO: | 6 |
| LpxOEcoRIfor | 5'-GCGAATTCATGTTCGCAGCAATCATT-3' | SEQ ID NO: | 7 |
| LpxOBamHIrev | 5'-GCGGATCCTCAGAGGAGGCTGAAAAG-3' | SEQ ID NO: | 8 |
| PagPBamHIfor | 5'-GCGGATCCATGAACGTGAGTAAATAT-3' | SEQ ID NO: | 9 |
| PagPNotIrev | 5'-GCGCGGCCGCTCAAAACTGAAAGCGCAT-3' | SEQ ID NO: | 10 |
| LpxRBamHIfor | 5'-GCGGATCCATGAACAAATACAGCTAT-3' | SEQ ID NO: | 11 |
| LpxRNotIrev | 5'-GCGCGGCCGCTCAGAAGAAGAAGGTGAT-3' | SEQ ID NO: | 12 |

Plasmid Construction and Growth Conditions

Each of the six genes, lpxE, lpxF, lpxO, lpxR, pagL, and pagP, were cloned individually into pQLinkN using the primers listed in Table 3, and combinatorial plasmids were generated as previously described (Scheich et al., 2007). Transformation of plasmids into BN1 and BN2 yielded the 61 strains listed in FIG. 2c and Table 1. All strains were grown at 37° C. in Luria-Bertani Broth (LB) or on LB agar supplemented with an optimized isopropyl β-D-1-thiogalactopyranoside (IPTG) concentration between 50 μM and 1 mM, which was determined by TLC analysis of enzyme activity (data not shown).

Isolation of Lipid A $^{32}$P radiolabeled lipid A was isolated from 7 ml cultures for analysis by TLC as previously described (Tran et al., 2006). Densitometry was calculated using Quantity One software. For MS, lipid A was prepared from 15 ml cultures as described previously (Hankins et al., 2011). Samples were analyzed using a MALDI-TOF/TOF (ABI 4700 Proteomics Analyzer) mass spectrometer as previously described (Touze et al., 2008). Lipid A profiles from each strain were analyzed by negative ion linear mode MS. However, in strains expressing both phosphatases, LpxE and LxpF, lipids were detected in the positive mode.

Isolation of LPS

LPS was isolated from 13 of the strains by phenol extraction and purified as previously described (Hankins et al., 2011). Quantification of each was achieved using the 3-deoxy-d-manno-octulosonic acid (Kdo) colorimetric assay to normalize the samples to 0.5 mg/ml using E. coli K12 LPS (LPS EK-Ultrapure, Invivogen) as a standard.

Whole Cell Bacterial Sample Preparation

Whole cells for assays were prepared by growing a diluted overnight culture to an OD$_{600}$ of 1.0 at 37° C. in LB containing 100 μg/ml ampicillin and 50 μM to 1 mM IPTG. Cells were washed in sterile phosphate buffered saline (PBS) to remove lysed cells or outer membrane vesicles. Cell pellets were gently resuspended in 5 mls of PBS, and the OD$_{600}$ was measured. 5×10$^9$ cells were harvested by centrifugation, gently resuspended in 1 ml PBS and aliquoted for storage at −80° C. CFU plating after storage at −80° C. confirmed equivalent cell counts between samples.

TLR Signaling Assays

HEK-Blue™ hTLR4, HEK-Blue™ hTLR2, and THP1-XBlue™-MD2-CD14 cell lines were purchased from Invivogen and maintained according to their specifications. Whole cell aliquots and LPS samples were thawed and serial diluted immediately prior to use in assays done as previously described (Hankins et al., 2011) with the following modification: whole cell stimulation assays were done in 30 μg/ml chloramphenicol instead of 50 U/ml-50 μg/ml Pen-Strep to maintain a bacteriostatic effect. At least two biological replicates were each done in triplicate and one representative set was shown here, normalized to data for the BN1 pQLinkN strain.

Lipopolysaccharide Stimulation Assays and Cytokine Quantification

THP-1 human monocytes (ATCC) were maintained according to ATCC's specifications. THP-1 monocytes were differentiated into macrophages by transferring cells into 24-well tissue culture plates at 1×10$^5$ cells/well in the presence of 50 ng/ml phorbol myristate acetate. Following incubation at 37° C. with 5% CO$_2$ for 36 h, the differentiated cells were washed with Hanks balanced salt solution (Invitrogen) and stimulated for 24 h with 10 and 100 ng/ml LPS. The culture supernatants from triplicate wells were harvested and sent to Ocean Ridge Biosciences (Palm Beach Gardens, Fla.) for detection and quantification of the following cytokines: TNF-α, IL-1β, IL-6, IL-8, G-CSF, RANTES and MCP-1.

Statistical Analysis

Statistical analysis was performed using one-tailed T-tests. P-values were calculated with an n≥3 and α=0.05 or 0.01, as reported in the figure legends of each data set. Error bars refer to standard deviation.

Construction of Two Mutants Producing Unmodified Lipid A

Figure 8A:
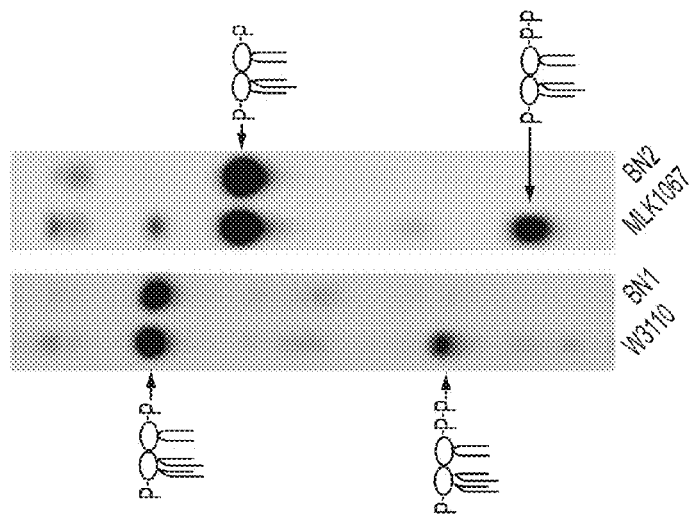

To produce an E. coli library with defined lipid A structures, two background strains that synthesize homogeneous, unmodified lipid A profiles were generated. (FIG. 8). Strain BN1 produces hexa-acylated, bis-phosphorylated lipid A, the highly endotoxic, major species synthesized by E. coli. BN1 was generated by deletion of genes that modify E. coli lipid A under normal growth conditions. Thin-layer chromatography (TLC) and MALDI-TOF mass spectrometry (MS) confirmed a homogeneous lipid A profile (FIGS. 8a, b). Deletion of lpxM in BN1 generated strain BN2, which synthesizes only penta-acylated lipid A (confirmed by TLC and MS analysis, FIGS. 8a, c). BN1 and BN2 provide two distinct templates suitable for alteration by endotoxin modifying enzymes.

Combinatorial Engineering of Lipid A

BN1 and BN2 were transformed with the pQLinkN vector harboring combinations of genes encoding the lipid A modification enzymes PagP, PagL, LpxR, LpxE, LpxF and LpxO. FIG. 2 summarizes each enzyme, its source organism, activity, and active site topology, along with the 61 strains engineered. Considering enzyme specificities, some combinations were omitted. For example, *Francisella* LpxF does not function on hexa-acylated lipid A substrate, so LpxF was not introduced into BN1. Additionally, *Salmonella* LpxO hydroxylates the 3'-acyloxyacyl chain, which is absent in BN2, precluding the use of LpxO in this strain.

The diversity of the 61 lipid A profiles was confirmed by TLC analysis of isolated $^{32}$P-labeled lipid A. FIG. 3a demonstrates the diversity of endotoxin species produced in BN1 and BN2 expressing combinations of lipid A modifying enzymes. 12 strains were selected to represent simple and complex strains (FIG. 3a), although all strains were confirmed by TLC (data not shown). In some strains, like BN2 pL, 99.2% of lipid A molecules are modified by PagL, while in other strains, like BN1 pP, PagP is less efficient. Many strains express multiple enzymes with various efficiency, so strains like BN2 pELPR produce a heterogeneous mixture of endotoxin (FIG. 3a).

Figure 3D:
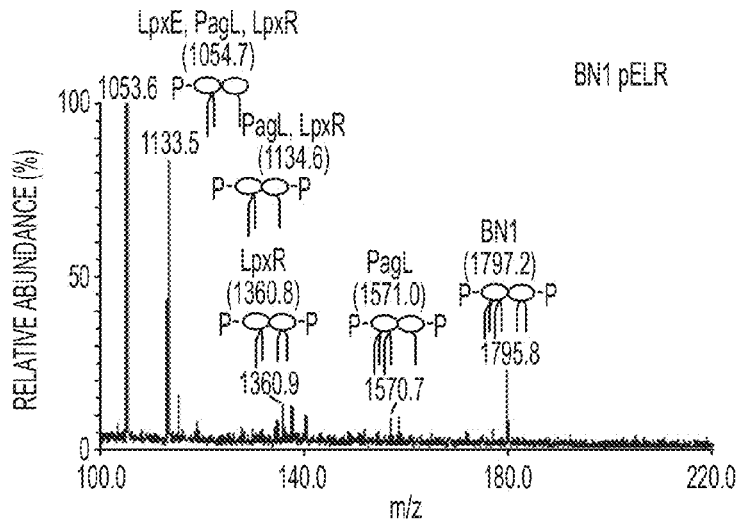

In addition to TLC, all strains were subjected to MS for structural identification (FIG. 9). Since each enzyme used has been previously characterized, mass changes can be anticipated, even in complex enzyme combinations. FIG. 3b-d highlights examples of MS results for three categories of strains: phosphate modified (b), acyl chain modified (c), or a combination (d). In FIG. 3b, the mass spectra of BN1 pE reveals a major peak at m/z 1716.8 corresponding to the removal of one phosphate group. In FIG. 3c, MS of BN1 pLR yields a major peak at m/z 1133.9 corresponding to a tri-acylated lipid A, resulting from deacylation by PagL and LpxR. The combination of the two modification classes can be seen in FIG. 3d, where the phosphatase LpxE is present with PagL and LpxR yielding a major peak at m/z 1053.6 corresponding to a tri-acylated mono-phosphorylated lipid A. Interestingly, these results exemplify *E. coli's* tolerance for drastic changes to its evolutionarily conserved lipid A profile.

Differential TLR4 Stimulation by Bacterial Cells with Modified Lipid A

To examine the range of immunogenicity of whole cells with diverse lipid A structures, TLR4 stimulation studies were conducted. In addition to phosphate and hydroxyl group modifications, both acyl chain position and acyl chain number were expected to play a role. The library yielded an array of stimulation, and 51 of the strains were found to be significantly different from the BN1 control at $10^4$ CFU/well (p<0.05). To directly compare all strains, the data is presented colorimetrically (FIG. 4, FIG. 10), and graphical data for each strain can be found in FIG. 11.

TLR4 stimulation by BN1 strains expressing a single enzyme generally did not differ from the BN1 background strain, even in BN1 pL, in which PagL cleaves the majority of the lipid A to penta-acylated form predicted to be less inflammatory (FIG. 4, FIG. 9). The strong TLR4 response of strains with only one enzyme indicates that a combinatorial approach might more effectively lower endotoxicity.

Interestingly, many enzyme combinations with low TLR4 stimulation could be elevated to intermediate levels by the addition of other enzymes. Some of these were predictable, such as BN1 pLPR. LpxR and PagL deacylase activities greatly reduce TLR4 stimulation in the precursor strain, BN1 pLR (FIG. 4a). When PagP is included to generate BN1 pLPR, TLR4 stimulation rises to an intermediate level because PagP increases acylation. However, in some strains an increase in TLR4 stimulation was unexpected. For example, BN2 induces a low TLR4 response that is increased when LpxF and PagL are expressed (BN2 pFL). This is surprising because removal of an acyl chain and phosphate group from BN2 was expected to further reduce the TLR4 stimulation. Moreover, when PagP is added (BN2 pFLP), the response increases further. This was unforeseen because PagP restores a penta-acylated lipid A that resembles the original, low stimulating BN2 strain, albeit with the acyl chain in a different position. Therefore, it appears TLR4 stimulation cannot be predicted solely from expected enzyme activity. The diversity of these results indicates that a strain inducing high, intermediate, or low TLR4 stimulation could be selected for particular purposes.

Engineered Strains Yield a Collection of LPS Samples with a Broad Range of TLR4 Activation To examine TLR4 stimulation by LPS, assays were performed using isolated LPS from 13 strains (FIG. 4b). The effects of several of the enzymes on LPS immunogenicity have been characterized individually (Kong et al., 2011 & Kawasaki et al., 2005), but the range of stimulation resulting from the library was surprisingly diverse. All LPS samples except BN1 pE were significantly lower than BN1 at 1 ng/ml (p<0.05), and a similar trend was observed between cells and purified LPS (FIG. 4).

Strain BN1 pELP, which produces lipid A that mimics MPL™, only differs significantly from the BN1 control at $10^3$-$10^4$ CFU/well in the whole cell assay and only at 0.1 ng/ml in the LPS assay (FIG. 4b). Although this LPS remains an activator of TLR4, the MS lipid A profile is remarkably similar to vaccine grade MPL™ prepared from *S. minnesota*, but no longer requires chemical treatment. BN1 pELP and another similar strain, BN1 pELOP, also show a higher percentage of the predominant species, 3-O-deacyl-4'-monophosphoryl lipid A, found in MPL™ (FIG. 13).

Previous reports have asserted that LPS isolated from certain gram-negatives (e.g. *Leptospira interrogans*) stimulates Toll-like receptor 2, (TLR2), which typically detects lipoproteins (Werts et al. 2001). However, TLR2 assays performed on the 13 LPS samples described above showed no stimulation, even at 1,000 ng/ml (data not shown).

Lipid A Modification is Sufficient to Reduce Stimulation of Monocytes Expressing Multiple Pattern Recognition Receptors To determine if modifying lipid A, and thus stimulation of TLR4, is sufficient to alter overall immune response, bacterial cells were incubated with THP1-XBlue-MD2-CD14 monocytes. These cells express all TLRs and NOD (nucleotide-oligomerization domain) proteins, recognizing conserved bacterial patterns such as flagellar proteins, lipoproteins, and peptidoglycan. Results for all strains were significantly lower than BN1 at $10^4$ CFU/well (p<0.05) (FIG. 5a). Strains with reduced TLR4 stimulation also had a reduced response in this assay. This confirms that alteration of the lipid A portion of LPS is sufficient to affect the overall response between $10^3$-$10^5$ CFU/well, regardless of other cell surface bacterial mediators of inflammation.

Cytokine Profile of Human Monocytes Stimulated by LPS

The cytokine profile of THP-1 monocytes following LPS stimulation was analyzed to further predict the potential immune response induced from the combinatorial strains. In particular, two major TLR4 pathways were investigated: the MyD88-Dependent and TRIF pathways (FIG. 5, FIG. 12). The MyD88 pathway activates the highly proinflammatory response to LPS, although some low level MyD88 induction is beneficial for long lasting immunity in vaccines. The TRIF pathway is less inflammatory yet remains an effective pathway for adaptive immune responses important to vaccine adjuvants.

To measure proinflammatory cytokines involved in the MyD88 TLR4 pathway, TNF-$\alpha$, IL-6, IL-1$\beta$, and IL-8 were quantified. A full spectrum of cytokine levels was observed (FIG. 5b), reflecting the results of the TLR4 assay using LPS. The TRIF pathway was detected by production of the cytokines G-CSF, RANTES, and MCP-1 (FIG. 5c). LPS from the BN1 background strain strongly stimulated all three cytokines, and LPS with engineered lipid A domains showed variation in cytokine production, with some cases of complete elimination.

Interestingly, some samples retained the capacity to stimulate certain cytokines while other cytokines were drastically reduced. For example, MCP-1 stimulation level of BN1 pLPR is 40% compared to the BN1 level, yet G-CSF production is almost completely abolished (FIG. 5c). Another instance of variable production of cytokines was observed in IL-8 levels. BN2 pEP, for example, stimulates IL-8 production equal to BN1, yet every other cytokine level is greatly diminished (FIG. 5b). These results indicate that the cytokine profile induced by modified LPS can be largely diverse, even within the limited fraction of the 61 engineered strains from which LPS was purified and studied.

Lipid A from Various Strains Induces a Strong Acquired Immune Response in Mice

To investigate the adjuvant potential of strains in this library, BALB/c mice were immunized with emulsions of the antigen Hen Egg Lysozyme (HEL) and purified lipid A from 4 strains, BN1 pELP, BN1 pPR, BN2 pEP, and BN1 pLPR. Compared to MPL™, all lipid formulations resulted in high anti-HEL IgG titers, and only BN2 pEP was significantly lower than MPL (FIG. 6). This indicates that the combinatorial strains could be a source for effective yet nontoxic adjuvants. The similar titers between lipid A samples, in contrast to the variation found in the human cytokine response, could be due to the lower specificity of the murine TLR4 than human TLR4 (data not shown).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. Pfeiffer, R. Untersuchungen uber das Choleragift. *Z Hygeine* 11, 393-412 (1892).
2. Poltorak, A., Ricciardi-Castagnoli, P., Citterio, S. & Beutler, B. Physical contact between lipopolysaccharide and toll-like receptor 4 revealed by genetic complementation. *Proceedings of the National Academy of Sciences of the United States of America* 97, 2163-2167 (2000).
3. Raetz, C. R. & Whitfield, C. Lipopolysaccharide endotoxins. *Annual review of biochemistry* 71, 635-700 (2002).
4. Raetz, C. R., Reynolds, C. M., Trent, M. S. & Bishop, R. E. Lipid A modification systems in gram-negative bacteria. *Annual review of biochemistry* 76, 295-329 (2007).
5. Park, B. S. et al. The structural basis of lipopolysaccharide recognition by the TLR4-MD-2 complex. *Nature* 458, 1191-1195 (2009).
6. Teghanemt, A., Zhang, D., Levis, E. N., Weiss, J. P. & Gioannini, T. L. Molecular basis of reduced potency of underacylated endotoxins. *Journal of immunology* 175, 4669-4676 (2005).
7. Lien, E. et al. Toll-like receptor 4 imparts ligand-specific recognition of bacterial lipopolysaccharide. *The Journal of clinical investigation* 105, 497-504 (2000).
8. Casella, C. R. & Mitchell, T. C. Putting endotoxin to work for us: monophosphoryl lipid A as a safe and effective vaccine adjuvant. *Cellular and molecular life sciences: CMLS* 65, 3231-3240 (2008).
9. Petrovsky, N. & Aguilar, J. C. Vaccine adjuvants: current state and future trends. *Immunology and cell biology* 82, 488-496 (2004).
10. Qureshi, N., Takayama, K. & Ribi, E. Purification and structural determination of nontoxic lipid A obtained from the lipopolysaccharide of Salmonella typhimurium. *The Journal of biological chemistry* 257, 11808-11815 (1982).
11. Persing, D. H. et al. Taking toll: lipid A mimetics as adjuvants and immunomodulators. *Trends in microbiology* 10, S32-37 (2002).
12. Chen, J., Tao, G. & Wang, X. Construction of an Escherichia coli mutant producing monophosphoryl lipid A. *Biotechnology letters* 33, 1013-1019 (2011).
13. Kawasaki, K., Ernst, R. K. & Miller, S. I. 3-O-deacylation of lipid A by PagL, a PhoP/PhoQ-regulated deacylase of Salmonella typhimurium, modulates signaling through Toll-like receptor 4. *The Journal of biological chemistry* 279, 20044-20048 (2004).
14. Keiser, P. B. et al. A phase 1 study of a meningococcal native outer membrane vesicle vaccine made from a group B strain with deleted lpxL1 and synX, over-expressed factor H binding protein, two PorAs and stabilized OpcA expression. *Vaccine* 29, 1413-1420 (2011).

15. Chen, G. et al. Oral delivery of tumor-targeting Salmonella exhibits promising therapeutic efficacy and low toxicity. *Cancer science* 100, 2437-2443 (2009).
16. Weiss, S. & Chakraborty, T. Transfer of eukaryotic expression plasmids to mammalian host cells by bacterial carriers. *Current opinion in biotechnology* 12, 467-472 (2001).
17. Bishop, R. E. et al. Transfer of palmitate from phospholipids to lipid A in outer membranes of gram-negative bacteria. *The EMBO journal* 19, 5071-5080 (2000).
18. Trent, M. S., Pabich, W., Raetz, C. R. & Miller, S. I. A PhoP/PhoQ-induced Lipase (PagL) that catalyzes 3-O-deacylation of lipid A precursors in membranes of *Salmonella typhimurium*. *The Journal of biological chemistry* 276, 9083-9092 (2001).
19. Reynolds, C. M. et al. An outer membrane enzyme encoded by *Salmonella typhimurium* lpxR that removes the 3'-acyloxyacyl moiety of lipid A. *The Journal of biological chemistry* 281, 21974-21987 (2006).
20. Wang, X., Karbarz, M. J., McGrath, S. C., Cotter, R. J. & Raetz, C. R. MsbA transporter-dependent lipid A 1-dephosphorylation on the periplasmic surface of the inner membrane: topography of francisella novicida LpxE expressed in *Escherichia coli*. *The Journal of biological chemistry* 279, 49470-49478 (2004).
21. Wang, X., McGrath, S. C., Cotter, R. J. & Raetz, C. R. Expression cloning and periplasmic orientation of the *Francisella novicida* lipid A 4'-phosphatase LpxF. *The Journal of biological chemistry* 281, 9321-9330 (2006).
22. Gibbons, H. S., Lin, S., Cotter, R. J. & Raetz, C. R. Oxygen requirement for the biosynthesis of the S-2-hydroxymyristate moiety in *Salmonella typhimurium* lipid A. Function of LpxO, A new Fe2+/alpha-ketoglutarate-dependent dioxygenase homologue. *The Journal of biological chemistry* 275, 32940-32949 (2000).
23. Kong, Q. et al. *Salmonella* Synthesizing 1-Monophosphorylated Lipopolysaccharide Exhibits Low Endotoxic Activity while Retaining Its Immunogenicity. *Journal of immunology* 187, 412-423 (2011).
24. Kawasaki, K., Ernst, R. K. & Miller, S. I. Purification and characterization of deacylated and/or palmitoylated lipid A species unique to *Salmonella enterica serovar Typhimurium*. *Journal of endotoxin research* 11, 57-61 (2005).
25. Werts, C. et al. Leptospiral lipopolysaccharide activates cells through a TLR2-dependent mechanism. *Nature immunology* 2, 346-352 (2001).
26. Ferreira, G. N., Monteiro, G. A., Prazeres, D. M. & Cabral, J. M. Downstream processing of plasmid DNA for gene therapy and DNA vaccine applications. *Trends in biotechnology* 18, 380-388 (2000).
27. Fiske, M. J., Fredenburg, R. A., VanDerMeid, K. R., McMichael, J. C. & Arumugham, R. Method for reducing endotoxin in Moraxella catarrhalis UspA2 protein preparations. *Journal of chromatography. B, Biomedical sciences and applications* 753, 269-278 (2001).
28. Liu, S. et al. Removal of endotoxin from recombinant protein preparations. *Clinical biochemistry* 30, 455-463 (1997).
29. Magalhaes, P. O. et al. Methods of endotoxin removal from biological preparations: a review. *Journal of pharmacy & pharmaceutical sciences: a publication of the Canadian Society for Pharmaceutical Sciences, Societe canadienne des sciences pharmaceutiques* 10, 388-404 (2007).
30. Przybylowski, M., Bartido, S., Borquez-Ojeda, O., Sadelain, M. & Riviere, I. Production of clinical-grade plasmid DNA for human Phase I clinical trials and large animal clinical studies. *Vaccine* 25, 5013-5024 (2007).
31. Grillo-Courvalin, C., Goussard, S. & Courvalin, P. Bacterial Vectors for Delivering Gene and Anticancer Therapies. *Microbe* 6, 115-121 (2011).
32. Rockwell, C. E., Morrison, D. C. & Qureshi, N. Lipid A-mediated tolerance and cancer therapy. *Advances in experimental medicine and biology* 667, 81-99 (2009).
33. Carswell, E. A. et al. An endotoxin-induced serum factor that causes necrosis of tumors. *Proceedings of the National Academy of Sciences of the United States of America* 72, 3666-3670 (1975).
34. Bertok, L. Radio-detoxified endotoxin activates natural immunity: a review. *Pathophysiology: the official journal of the International Society for Pathophysiology/ISP* 12, 85-95 (2005).
35. Akimoto, T., Kumazawa, E., Jimbo, T., Joto, N. & Tohgo, A. Antitumor effect of DT-5461a, a synthetic low-toxicity lipid A analog, involves endogenous tumor necrosis factor induction subsequent to macrophage activation. *International journal of immunopharmacology* 16, 887-893 (1994).
36. Peri, F. & Piazza, M. Therapeutic targeting of innate immunity with Toll-like receptor 4 (TLR4) antagonists. *Biotechnology advances* (2011).
37. Geurtsen, J. et al. Supplementation of whole-cell pertussis vaccines with lipopolysaccharide analogs: modification of vaccine-induced immune responses. *Vaccine* 26, 899-906 (2008).
38. Reynolds, C. M. & Raetz, C. R. Replacement of lipopolysaccharide with free lipid A molecules in Escherichia coli mutants lacking all core sugars. *Biochemistry* 48, 9627-9640 (2009).
39. Herrera, C. M., Hankins, J. V. & Trent, M. S. Activation of PmrA inhibits LpxT-dependent phosphorylation of lipid A promoting resistance to antimicrobial peptides. *Molecular microbiology* 76, 1444-1460 (2010).
40. Baba, T. et al. Construction of *Escherichia coli* K-12 in-frame, single-gene knockout mutants: the Keio collection. *Molecular systems biology* 2, 2006 0008 (2006).
41. Datsenko, K. A. & Wanner, B. L. One-step inactivation of chromosomal genes in *Escherichia coli* K-12 using PCR products. *Proceedings of the National Academy of Sciences of the United States of America* 97, 6640-6645 (2000).
42. Touze, T., Tran, A. X., Hankins, J. V., Mengin-Lecreulx, D. & Trent, M. S. Periplasmic phosphorylation of lipid A is linked to the synthesis of undecaprenyl phosphate. *Molecular microbiology* 67, 264-277 (2008).
43. Tran, A. X. et al. The lipid A 1-phosphatase of Helicobacter pylori is required for resistance to the antimicrobial peptide polymyxin. *Journal of bacteriology* 188, 4531-4541 (2006).
44. Scheich, C., Kummel, D., Soumailakakis, D., Heinemann, U. & Bussow, K. Vectors for co-expression of an unrestricted number of proteins. *Nucleic acids research* 35, e43 (2007).
45. Hankins, J. V. et al. Elucidation of a novel Vibrio cholerae lipid A secondary hydroxy-acyltransferase and its role in innate immune recognition. *Molecular microbiology* (2011).
46. Marolda, C. L., Lahiry, P., Vines, E., Saldias, S. & Valvano, M. A. Micromethods for the characterization of lipid A-core and O-antigen lipopolysaccharide. *Methods in molecular biology* 347, 237-252 (2006).
47. Karow, M. & Georgopoulos, C. Isolation and characterization of the *Escherichia coli* msbB gene, a multicopy suppressor of null mutations in the high-temperature requirement gene htrB. *Journal of bacteriology* 174, 702-710 (1992).

What is claimed is:

1. An isolated engineered strain of *E. coli* comprising deletions of lpxT, eptA and pagP genes, said *E. coli* comprising immunologically active lipid A on its surface.

2. The isolated engineered strain of claim 1 further comprising deletions of the Kan$^R$ cassette and lpxM gene.

3. The isolated engineered strain of claim 1 further comprising at least one expression vector that comprises at least one gene encoding a lipid A modification enzyme, wherein the gene encoding a lipid A modification enzyme is selected from the group consisting of lpxE, lpxF, lpxO, lpxR, pagL, and pagP.

4. The isolated engineered strain of claim 2 further comprising at least one expression vector that comprises at least one gene encoding a lipid A modification enzyme, wherein the gene encoding a lipid A modification enzyme is selected from the group consisting of lpxE, lpxF, lpxO, lpxR, pagL, and pagP.

5. An isolated engineered strain of *E. coli* comprising deletions of lpxT, eptA, and pagP genes and further comprising an expression vector that comprises lpxE, pagL, pagP, said *E. coli* comprising immunologically active lipid A on its surface.

6. An isolated engineered strain of *E. coli* comprising deletions of lpxT, eptA, and pagP genes and further comprising an expression vector that comprises lpxE, pagL, lpxO, pagP, said *E. coli* comprising immunologically active lipid A on its surface.

7. A method for synthesizing 3-O-deacyl-4'-monophosphoryl lipid A without the need for acid and base treatment of the synthesized lipid A comprising:
providing at least one isolated engineered bacterium of *E. coli* according to claim 1;
introducing the bacterium to a plasmid comprising an expression vector that comprises lpxE, pagL, pagP or an expression vector that comprises lpxE. pagL, lpxO, pagP;
allowing the engineered bacterium to grow under conditions to produce 3-O-deacyl-4'-monophosphoryl lipid A.

8. A lipopolysaccharide purified from the isolated engineered strain of claim 3.

9. A lipopolysaccharide purified from the isolated engineered strain of claim 4.

10. A vaccine adjuvant comprising a lipopolysaccharide purified from the isolated engineered strain of claim 3.

11. A vaccine adjuvant comprising a lipopolysaccharide purified from the isolated engineered strain of claim 4.

12. A whole cell immunogenic composition comprising the isolated engineered strain of claim 3 and a pharmaceutically acceptable excipient or carrier.

13. A whole cell immunogenic composition comprising the isolated engineered strain of claim 4 and a pharmaceutically acceptable excipient or carrier.

* * * * *